United States Patent [19]
Arnold, Jr. et al.

[11] Patent Number: 5,854,410
[45] Date of Patent: Dec. 29, 1998

[54] OLIGONUCLEOSIDE CLEAVAGE COMPOUNDS AND THERAPIES

[75] Inventors: Lyle J. Arnold, Jr., Poway; Mark A. Reynolds, San Diego; David A. Schwartz, Encinitas; William J. Daily, San Diego, all of Calif.

[73] Assignee: Genta Incorporated, San Diego, Calif.

[21] Appl. No.: 223,355

[22] Filed: Mar. 31, 1994

[51] Int. Cl.$^6$ .......................... C07H 21/00; C07H 21/04; C12Q 1/68

[52] U.S. Cl. ............................ 536/23.1; 435/6; 536/24.3; 536/24.5

[58] Field of Search ........................ 435/6, 91.1; 514/44; 536/23.1, 24.1, 24.3, 24.5

[56] References Cited

FOREIGN PATENT DOCUMENTS

| | | |
|---|---|---|
| 92/02532 | 2/1992 | WIPO . |
| WO/93 17717 | 9/1993 | WIPO . |

OTHER PUBLICATIONS

Distefano et al. "Cooperative binding of oligonucleotides to DNA by triple helix formation: Dimerization via Watson Crick hydrogen bonds" J. Am. Chem. Soc. 113: 590–5902, (1991).

Lin et al. "Use fo EDTA derivatization to characterize ineractions between oligodeoxyribonucleoside mehtylphosphonates and nucleic acids" Biochemistry 28: 1054–1061, (1989).

Reynolds et al "A non–nucleotide–based linking method for the preparation of psoalen–derivatized methylphosphonate oligonucleosides" Bioconjugate Chem. 3(5): 366–374, (Oct. 1992).

Chu et al. Nonenzymatic sequence–specific cleavage of single–stranded DNA Proc. Natl. Acad. Sci. USA 82: 963–967, (Feb. 1985).

Dreyer et al. Sequence–specific cleavage of single–stranded DNA: Oligodeoxynucleotide–EDTA–FE(II). Proc. Natl. Acad. Sci. USA 82: 968–972, (Feb. 1985).

Goodchild "Conjugates of oligonucleotides and modified oligonucleoitdes: A review of their synthesis and properties" Bioconjugate Chem. 1(3): 165–187, (Jun. 1990).

Agris, et al., "Inhibition of Vesicular Stomatitis Virus Protein Synthesis and Infection by Sequence–Specific Oligodeoxyribonucleoside Methylphosphonates," *Biochemistry* 23, 6268–6275 (1986).

Anslyn & Breslow, "On the Mechanism of Catalysis by Ribonuclease, " *J. Am. Chem. Soc.* 111, 4473–4482 (1989).

Ariga & Anslyn, "Manipulating the Stoichiometry and Strength of Phosphodiester Binding to a Bisguanidine Cleft in DMSO/Water Solutions," *J. Org. Chem.* 57, 417–419 (1992).

Baker, "Decapitation' of a 5'–Capped Oligoribonucleotide by o–Phenanthroline:Cu(II)," *J. Am. Chem. Soc.* 115, 3378–3379 (1993).

Blake, et al., "Hybridization Arrest of Globin Synthesis in Rabbit Reticulocyte Lysates and Cells by Oligodeoxyribonucleoside Methylphosphonates," *Biochemistry* 24, 6139–6145 (1985).

Blake, et al., "Inhbition of Rabbit Globin mRNA Translation by Sequence–Specific Oligodeoxyribonucleotides," *Biochemistry* 24, 6132–6138 (1985).

Corey & Schultz, "Generation of a Hybrid Sequence–Specific Single Stranded Deoxyribonuclease," *Science* 238, 1401–1403 (1987).

Jubian, et al., "Molecular Recognition and Catalysis," *J. Am. Chem. Soc.* 114, 1120–1121 (1992).

Miller, et al., "Control of Ribonucleic Acid Function by Oligonucleoside Methylphosphonates," *Biochimie* 67, 769–776 (1985)).

Morrow, et al., "Efficient Catalytic Cleavage of RNA by Lanthanide(III) Macrocyclic Complexes: Toward Synthetic Nucleases for in Vivo Applications," *J. Am. Chem. Soc.* 114, 1903–1905 (1992).

Morrow & Chin, "Synthesis and Dynamic Properties of Kinetically Inert Lanthanide Compounds," *Inorg. Chem.* 32, 3357–3361 (1993).

Moser & Dervan, "Sequence–Specific Cleavage of Double Helical DNA by Triple Helix Formation," *Science* 238, 645–650 (1987).

Murakami, et al., "Characterization of Sequence–Specific Oligodeoxyribonucleoside Methylphosphonates and Their Interaction with Rabbit Globin mRNA,"*Biochemistry* 24, 4041–4046 (1985).

Perreault, et al., "Mixed Deoxyribo–and Ribo–oligonucleotides with Catalytic Activity," *Nature* 344, 565–567 (1990).

Podyminogin, et al., "Synthetic RNA–cleaving Molecules Mimicking Ribonuclease A Active Center," *Nucleic Acids Research* 21, 5950–5956 (1993).

(List continued on next page.)

*Primary Examiner*—John L. LeGuyader
*Assistant Examiner*—Thomas G. Larson
*Attorney, Agent, or Firm*—Knobbe, Martens, Olson & Bear, LLP

[57] ABSTRACT

Methods and compounds for selective cleavage of nucleic acid are described. The compounds generally contain three functionalities: (1) an oligonucleoside portion which is substantially complementary to at least a portion of the target nucleic acid, thereby providing selectivity to the compound; (2) a non-complementary portion which replaces one of the otherwise-complementary nucleoside bases in the oligonucleoside and which serves to place the target nucleic acid strand into a conformation that favors the cleavage of a phosphodiester linkage opposite the non-complementary portion; and (3) a cleavage moiety which possesses one or more and preferably two or more of the features of (a) proton donation, (b) proton acceptance, (c) hydrogen bonding, (d) charge neutralization and (e) Lewis acidity. These compounds may be used for the study and treatment of diseases involving foreign genetic materials or alterations to or inappropriate expression of genomic DNA.

2 Claims, 3 Drawing Sheets

OTHER PUBLICATIONS

Shelton & Morrow, "Catalytic Transesterification and Hydrolysis of RNA by Zinc(II) Complexes," *Inorg. Chem.* 30, 4295–4299 (1991).

Smith, et al., "Enhanced Imidazole–Catalyzed RNA Cleavage Induced by a Bis–Alkylguanidinium Receptor," *J. Am. Chem. Soc.* 115, 362–364 (1993).

Steitz & Steitz, "A general Two–metal–ion Mechanism for Catalytic RNA," *Proc. Natl. Acad. Sci. USA* 90, 6498–6502 (1993).

Uhlmann & Peyman, "Antisense Oligonucleotides," *Chemical Reviews* 90, 544–584 (1990).

Usher & McHale, "Hydrolytic Stability of Helical RNA," *Proc. Nat. Acad. Sci. USA* 73, 1149–153 (1976).

Yoshinari, et al., "Oligoamines as Simple and Efficient Catalysts for RNA Hydrolysis," *J. Am. Chem. Soc.* 113, 5899–5901 (1991).

Wichstrom et al., "Human promyelocytic leukemia HL–60 cell proliferation and c–myc protein expression are inhibited by an antisense pentadecadeoxynucleotide targeted against c–myc RNA," Proc. Natl. Acad. Sci. USA, 85(4):1028–1032 (1988).

Krinke et al., "The Cleavage specificity of RNase III," Nucleic Acids Research, 18(16):4809–4815 (1990).

Hjalt et al., "Bulged–out nucleotides in an antisense RNA are required for the rapid target RNA binding in vitro and inhibition in vivo," Nucleic Acids Research, 23(4):580–587 (1995).

Hjalt et al., "Bulged–out nucleotides protect an antisense RNA from RNase III cleavage," Nucleic Acids Research, 23(4):571–579 (1995).

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: Yes ( i v ) ANTI-SENSE: Yes ( i x ) FEATURE:
        ( A ) NAME/KEY: cleavage compound
        ( C ) IDENTIFICATION METHOD: complementarity to SEQ ID NO:2
        ( D ) OTHER INFORMATION: cleavage by SEQ ID NO:2

( x i ) SEQUENCE DESCRIPTION: SEQ ID NO:1:

TAGCTTCCTT NGCTCCTG         18

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: Yes ( i v ) ANTI-SENSE: No ( i x ) FEATURE:
        ( A ) NAME/KEY: target strand R197- 1
        ( C ) IDENTIFICATION METHOD: complementarity to SEQ ID NO:1
        ( D ) OTHER INFORMATION: cleavage by SEQ ID NO:1

( x i ) SEQUENCE DESCRIPTION: SEQ ID NO:2:

CAGGAGCUAA GGAAGCUA         18

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: Yes ( i v ) ANTI-SENSE: Yes ( i x ) FEATURE:
    ( A ) NAME/KEY: cleavage compound
    ( C ) IDENTIFICATION METHOD: complementarity to SEQ ID NO:4
    ( D ) OTHER INFORMATION: cleavage by SEQ ID NO:4

( x i ) SEQUENCE DESCRIPTION: SEQ ID NO:3:

TAGCTTCCTT AGCTCCTG       18

( 2 ) INFORMATION FOR SEQ ID NO:4:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: Yes ( i v ) ANTI-SENSE: No ( i x ) FEATURE:
    ( A ) NAME/KEY: target strand R336
    ( C ) IDENTIFICATION METHOD: complementarity to SEQ ID NO:3
    ( D ) OTHER INFORMATION: cleavage by SEQ ID NO:3

( x i ) SEQUENCE DESCRIPTION: SEQ ID NO:4:

CAGGAGCUAA UGGAAGCUA       19

( 2 ) INFORMATION FOR SEQ ID NO:5:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: Yes ( i v ) ANTI-SENSE: Yes ( i x ) FEATURE:
    ( A ) NAME/KEY: tandem cleavage compound
    ( C ) IDENTIFICATION METHOD: complementarity to SEQ ID NO:7
    ( D ) OTHER INFORMATION: cleavage by SEQ ID NO:7

( x i ) SEQUENCE DESCRIPTION: SEQ ID NO:5:

NGTTAGCTCC TG       12

( 2 ) INFORMATION FOR SEQ ID NO:6:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: other nucleic acid ( i i i ) HYPOTHETICAL: Yes ( i v ) ANTI-SENSE: Yes ( i x ) FEATURE:

-continued

```
            ( A ) NAME/KEY: tandem cleavage compound
            ( C ) IDENTIFICATION METHOD: complementarity to SEQ ID NO:7
            ( D ) OTHER INFORMATION: cleavage by SEQ ID NO:7

( x i ) SEQUENCE DESCRIPTION: SEQ ID NO:6:
```

CACTCTTAGC TN                        12

( 2 ) INFORMATION FOR SEQ ID NO:7:

```
    ( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: other nucleic acid ( i i i ) HYPOTHETICAL: Yes ( i v ) ANTI-SENSE: No ( i x ) FEATURE:
            ( A ) NAME/KEY: target strand
            ( C ) IDENTIFICATION METHOD: complementarity to SEQ ID NOS:5
                    and 6
            ( D ) OTHER INFORMATION: cleavage by SEQ ID NOS:5 and 6

( x i ) SEQUENCE DESCRIPTION: SEQ ID NO:7:
```

CAGGAGCUAA CCGAGCUAAG AGUG                        24

( 2 ) INFORMATION FOR SEQ ID NO:8:

```
    ( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i i ) MOLECULE TYPE: other nucleic acid ( i i i ) HYPOTHETICAL: Yes ( i v ) ANTI-SENSE: No ( x i ) SEQUENCE DESCRIPTION: SEQ ID NO:8:
```

CAGGAGCUUA CGGAGCUACG AGUGAGU                        27

( 2 ) INFORMATION FOR SEQ ID NO:9:

```
    ( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: other nucleic acid ( i i i ) HYPOTHETICAL: Yes ( i v ) ANTI-SENSE: Yes ( i x ) FEATURE:
            ( A ) NAME/KEY: cleavage compound
            ( C ) IDENTIFICATION METHOD: complementarity to SEQ ID NO:2
            ( D ) OTHER INFORMATION: cleavage by SEQ ID NO:2

( x i ) SEQUENCE DESCRIPTION: SEQ ID NO:9:
```

NAGCTTCCTT AGCTCCTG                        18

( 2 ) INFORMATION FOR SEQ ID NO:10:

```
    ( i ) SEQUENCE CHARACTERISTICS:
```

( A ) LENGTH: 18 base pairs
( B ) TYPE: nucleic acid
( C ) STRANDEDNESS: single
( D ) TOPOLOGY: linear ( i i ) MOLECULE TYPE: other nucleic acid ( i i i ) HYPOTHETICAL: Yes ( i v ) ANTI-SENSE: Yes ( i x ) FEATURE:
( A ) NAME/KEY: cleavage compound
( C ) IDENTIFICATION METHOD: complementarity to SEQ ID NO:2
( D ) OTHER INFORMATION: cleavage by SEQ ID NO:2

( x i ) SEQUENCE DESCRIPTION: SEQ ID NO:10:

TAGCTTCCTT NNCTCCTG                18

( 2 ) INFORMATION FOR SEQ ID NO:11:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other nucleic acid ( i i i ) HYPOTHETICAL: Yes ( i v ) ANTI-SENSE: No ( i x ) FEATURE:
( A ) NAME/KEY: target strand
( C ) IDENTIFICATION METHOD: complementarity to SEQ ID NOS:5
and 6
( D ) OTHER INFORMATION: cleavage by SEQ ID NOS:5 and 6

( x i ) SEQUENCE DESCRIPTION: SEQ ID NO:11:

CAGGAGCUAA CGGAGCUAAG AGUG                24

( 2 ) INFORMATION FOR SEQ ID NO:12:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid ( i i i ) HYPOTHETICAL: Yes ( i v ) ANTI-SENSE: Yes ( i x ) FEATURE:
( A ) NAME/KEY: tandem cleavage compound
( C ) IDENTIFICATION METHOD: complementarity to SEQ ID
NOS:13 and 14
( D ) OTHER INFORMATION: cleavage by SEQ ID NO:14

( x i ) SEQUENCE DESCRIPTION: SEQ ID NO:12:

TAGCTTCCTN AGCTCCTG                18

( 2 ) INFORMATION FOR SEQ ID NO:13:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid (  i i i  ) HYPOTHETICAL: Yes (  i v  ) ANTI-SENSE: Yes (  i x  ) FEATURE:
    ( A ) NAME/KEY: tandem cleavage compound
    ( C ) IDENTIFICATION METHOD: complementarity to SEQ ID
        NOS:12 and 14
    ( D ) OTHER INFORMATION: cleavage by SEQ ID NO:14

(  x i  ) SEQUENCE DESCRIPTION: SEQ ID NO:13:

TAGCCTCCGA GGAAGCTA 18

( 2 ) INFORMATION FOR SEQ ID NO:14:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear (  i i  ) MOLECULE TYPE: other nucleic acid (  i i i  ) HYPOTHETICAL: Yes (  i v  ) ANTI-SENSE: No (  i x  ) FEATURE:
        ( A ) NAME/KEY: target strand
        ( C ) IDENTIFICATION METHOD: complementarity to SEQ ID
            NOS:12 and 13
        ( D ) OTHER INFORMATION: cleavage by SEQ ID NOS:12 and 13

( x i ) SEQUENCE DESCRIPTION: SEQ ID NO:14:

CAGGAGCUAU CGGAGGCUA 19

( 2 ) INFORMATION FOR SEQ ID NO:15:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear (  i i  ) MOLECULE TYPE: other nucleic acid (  i i i  ) HYPOTHETICAL: Yes (  i v  ) ANTI-SENSE: Yes (  i x  ) FEATURE:
        ( A ) NAME/KEY: tandem cleavage compound
        ( C ) IDENTIFICATION METHOD: complementarity to SEQ ID NO:13
        ( D ) OTHER INFORMATION: cleavage by SEQ ID NO:14

( x i ) SEQUENCE DESCRIPTION: SEQ ID NO:15:

TAGCTTCCTN 10

( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear (  i i  ) MOLECULE TYPE: other nucleic acid (  i i i  ) HYPOTHETICAL: Yes (  i v  ) ANTI-SENSE: Yes (  i x  ) FEATURE:

( A ) NAME/KEY: tandem cleavage compound
( C ) IDENTIFICATION METHOD: triple- strand complementarity to
    SEQ ID NOS:17 and 18
( D ) OTHER INFORMATION: cleavage by SEQ ID NO:18

( x i ) SEQUENCE DESCRIPTION: SEQ ID NO:16:

CCTTCCTTNC CTCCT                                                                        15

( 2 ) INFORMATION FOR SEQ ID NO:17:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: Yes ( i v ) ANTI-SENSE: Yes ( i x ) FEATURE:
        ( A ) NAME/KEY: tandem cleavage compound
        ( C ) IDENTIFICATION METHOD: triple- strand complementarity to
            SEQ ID NOS:16 and 18
        ( D ) OTHER INFORMATION: cleavage by SEQ ID NO:18

( x i ) SEQUENCE DESCRIPTION: SEQ ID NO:17:

AGGAGGNAAG GAAGG                                                                        15

( 2 ) INFORMATION FOR SEQ ID NO:18:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: Yes ( i v ) ANTI-SENSE: No ( i x ) FEATURE:
        ( A ) NAME/KEY: target strand
        ( C ) IDENTIFICATION METHOD: triple- strand complementarity to
            SEQ ID NOS:16 and 17
        ( D ) OTHER INFORMATION: cleavage by SEQ ID NOS:16 and 17

( x i ) SEQUENCE DESCRIPTION: SEQ ID NO:18:

UCCUCCCUUC CUUCC                                                                        15

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: Yes ( i v ) ANTI-SENSE: Yes ( i x ) FEATURE:
        ( A ) NAME/KEY: tandem cleavage compound
        ( C ) IDENTIFICATION METHOD: complementarity to SEQ ID
            NOS:20, 21 and 22
        ( D ) OTHER INFORMATION: cleavage by SEQ ID NO:22

( x i ) SEQUENCE DESCRIPTION: SEQ ID NO:19:

TCCTTTCCTC TGCTCCTG                                                                                          18

( 2 ) INFORMATION FOR SEQ ID NO:20:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: Yes ( i v ) ANTI-SENSE: Yes ( i x ) FEATURE:
        ( A ) NAME/KEY: tandem cleavage compound
        ( C ) IDENTIFICATION METHOD: complementarity to SEQ ID
            NOS:19 and 21
        ( D ) OTHER INFORMATION: cleavage by SEQ ID NO:22

( x i ) SEQUENCE DESCRIPTION: SEQ ID NO:20:

NTCTCCTTTC CT                                                                                                12

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: Yes ( i v ) ANTI-SENSE: Yes ( i x ) FEATURE:
        ( A ) NAME/KEY: tandem cleavage compound
        ( C ) IDENTIFICATION METHOD: complementarity to SEQ ID
            NOS:19, 20 and 22
        ( D ) OTHER INFORMATION: cleavage by SEQ ID NO:22

( x i ) SEQUENCE DESCRIPTION: SEQ ID NO:21:

TAGCTTCCTG AGAGGAAAGG A                                                                                      21

( 2 ) INFORMATION FOR SEQ ID NO:22:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: Yes ( i v ) ANTI-SENSE: No ( i x ) FEATURE:
        ( A ) NAME/KEY: target strand
        ( C ) IDENTIFICATION METHOD: complementarity to SEQ ID
            NOS:19 and 21
        ( D ) OTHER INFORMATION: cleavage by SEQ ID NOS:19, 20 and 21

( x i ) SEQUENCE DESCRIPTION: SEQ ID NO:22:

CAGGAGCUCA GGAAGCUA                                                                                          18

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: Yes (iv) ANTI-SENSE: No (ix) FEATURE:
        (A) NAME/KEY: R183
        (D) OTHER INFORMATION: target strand (xi) SEQUENCE DESCRIPTION: SEQ ID NO:23:

ACUCUCUCUC UCUCUCUCUG     20

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: Yes (iv) ANTI-SENSE: Yes (ix) FEATURE:
        (A) NAME/KEY: 1634-1
        (D) OTHER INFORMATION: complementarity to SEQ ID NO:2

(xi) SEQUENCE DESCRIPTION: SEQ ID NO:24:

TAGCTTCCTT AGCTCCTG     18

(2) INFORMATION FOR SEQ ID NO:25:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: Yes (iv) ANTI-SENSE: Yes (ix) FEATURE:
        (A) NAME/KEY: cleavage compound 1719-1
        (C) IDENTIFICATION METHOD: complementarity to SEQ ID NO:2
        (D) OTHER INFORMATION: cleavage by SEQ ID NO:2

(xi) SEQUENCE DESCRIPTION: SEQ ID NO:25:

TAGCTTCCTT GCTCCTG     17

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (i i i) HYPOTHETICAL: Yes (i v) ANTI-SENSE: Yes (i x) FEATURE:
    (A) NAME/KEY: cleavage compounds 2338-1, 2173-1
    (C) IDENTIFICATION METHOD: complementarity to SEQ ID NO:4
    (D) OTHER INFORMATION: cleavage by SEQ ID NO:4

(x i) SEQUENCE DESCRIPTION: SEQ ID NO:26:

TAGCTTCNTT AGCTCCTG                                                    18

(2) INFORMATION FOR SEQ ID NO:27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: other nucleic acid (i i i) HYPOTHETICAL: Yes (i v) ANTI-SENSE: No (i x) FEATURE:
        (A) NAME/KEY: target strand R320- 2

(x i) SEQUENCE DESCRIPTION: SEQ ID NO:27:

CAUGCAGGAG CUAAGGAAGC UA                                               22

OLIGONUCLEOSIDE CLEAVAGE COMPOUNDS AND THERAPIES

TECHNICAL FIELD

The present invention relates to the selective cleavage of nucleic acid using a cleavage compound. Inhibition of messenger RNA translation can be achieved by the hybridization of an anti-sense cleavage-enhancing oligonucleoside to a target nucleic acid, which then acts to cleave the nucleic acid at the target site.

BACKGROUND OF THE INVENTION

The possibility of developing therapeutic agents which bind to critical regions of RNA, for example mRNA, and selectively inhibit the function, replication or survival of abnormal cells or foreign organisms is an exciting concept. See, e.g., Dervan, *Science* 1988; 232:464–471. Various laboratories have pursued the design and development of molecules which interact with DNA in a sequence-specific manner. Such molecules have been proposed to have far-reaching implications for the diagnosis and treatment of diseases involving foreign genetic materials (such as viruses) or alterations to genomic DNA (such as cancer).

Anti-sense oligonucleotides are one type of sequence-specific molecule that has been demonstrated to be effective for inhibition of virus and human genes. In one application of this technology, anti-sense oligonucleotides are complementary to at least a portion of the messenger RNA (mRNA) transcribed from the target gene and can hybridize with the mRNA, thereby preventing ribosomal translation and subsequent protein synthesis. Anti-sense oligonucleotides have been shown to mediate inhibition of the Rous Sarcoma virus in tissue cultures (Zamecnik and Stephenson, *Proc. Natl. Sci. U.S.A.* 1978; 75:280–284) as well as the HTLV-III (HIV-1) virus (Zamecnik, et al., *Proc. Natl. Acad. Sci. U.S.A.* 1986; 83:4145–4146). Anti-sense oligonucleotides also have been shown to suppress the expression of selected non-viral genes in vitro, such as rabbit-globin (Goodchild, et al., *Arch. Biochem. Biophys.* 1988; 264:401–409) and human c-myb (Anfossi, et al., *Proc. Natl. Acad. Sci. U.S.A.* 1989; 86:3379).

Naturally-occurring oligonucleotides are subject to degradation or inactivation by cellular endogenous nucleases. Since anti-sense oligonucleotides must remain intact to be effective, some researchers have modified oligonucleotides to make them resistant to degradation or inactivation by nucleases. These modified oligonucleotides typically contain altered internucleoside linkages in which one or more of the naturally occurring phosphodiester linkages has been replaced. Oligonucleosides having phosphoroamidate or phosphorothioate linkages have been shown to increase the inhibition of HIV-1 in tissue cultures. See, e., Agarwal, et al., *Proc. Natl. Acad. Sci. U.S.A.* 1988; 85:7079–7083.

Nuclease-resistant nonionic oligonucleosides having methylphosphonate linkages have also been studied in vitro and in vivo as potential anticancer, antiviral and antibacterial agents. Miller, et al., Anti-Cancer Drug Design, 2:117–128 (1987). For example, anti-sense oligonucleosides containing methylphosphonate linkages have been demonstrated to inhibit HIV-induced syncytium formation. Sarin, et al., *Proc. Natl. Acad. Sci. U.S.A.* 1988; 85:7448–7451. The internucleoside bonds of these analogs are said to approximate the conformation of phosphodiester bonds in nucleic acids. It has been noted that the nucleic acid phosphate backbone in a methylphosphonate linkage is rendered neutral by methyl substitution of one anionic phosphoryl oxygen. This substitution is thought to decrease inter- and intra-strand repulsion attributable to charged phosphate groups. Miller, et al., Anti-Cancer Drug Design 2:117–128 (1987).

Oligonucleotide analogs with a methylphosphonate backbone are believed to be capable of penetrating living cells and have been reported to inhibit mRNA translation in globin synthesis and vesicular stomatitis viral protein synthesis and to inhibit herpes simplex virus replication by preventing splicing of pre-mRNA. Blake, et al., *Biochemistry* 1985; 24:6132–6138; Blake, et al., *Biochemistry* 1985; 24:6139–6145; Murakami, et al., *Biochemistry* 1985; 24:4041–4046; Miller, et al., *Biochimie* 1985; 67:769–776; Agris, et al., *Biochemistry* 1986; 23:6268–6275. Mechanisms of action for inhibition by the methylphosphonate analogs include formation of stable complexes with RNA and/or DNA having a substantially complementary nucleic acid sequence.

Nonionic oligonucleotide alkyl- and aryl-phosphonate analogs complementary to a selected single stranded foreign nucleic acid sequence are reported to be able to selectively inhibit the function or expression of that particular nucleic acid by binding to or interfering with that nucleic acid, without disturbing the function or expression of other nucleic acid present in the cell. See, e.g., U.S. Pat. Nos. 4,469,863 and 4,511,713. The use of complementary nuclease-resistant nonionic oligonucleoside methylphosphonates which are taken up by mammalian cells to inhibit viral protein synthesis in certain contexts, including herpes simplex virus-1, is described in U.S. Pat. No. 4,757,055.

The inhibition of infection of cells by HTLV-III by administration of oligonucleotides complementary to highly conserved regions of the HTLV-III genome necessary for HTLV-III replication and/or expression is reported in U.S. Pat. No. 4,806,463. The oligonucleotides were said to affect viral replication and/or gene expression as assayed by reverse transcriptase activity (replication) and production of viral proteins p1 5 and p24 (gene expression).

Anti-sense oligonucleotides or phosphorothioate or other analogs complementary to a sequence of viral RNA theoretically may be employed to interrupt the transcription and translation of viral mRNA into protein. The anti-sense constructs can bind to viral mRNA and obstruct ribosomes from moving along the mRNA, thereby halting the translation of mRNA into protein. This process is called "translation arrest" or "ribosomal-hybridization arrest." Yarochan, et al., "AIDS Therapies", Scientific American, pages 110–119 (October, 1988).

However, in practice, the use of an anti-sense hybridizing sequence to obstruct the ribosome from reading along the mRNA is not generally useful in the coding portion of the target mRNA, since an anti-sense sequence targeted to the coding portion is often removed from hybridization with the target sequence during the course of translation, even where the binding constant is high. In contrast, an anti-sense sequence targeted to the 5'-untranslated position of a mRNA molecule may achieve translation arrest through a blocking type mechanism. Nevertheless, it is useful in a variety of contexts to attempt to target the coding portion of a target mRNA (as opposed to an untranslated region) in order to prevent translation. For example, it may be necessary to target the coding sequence where it is desired to inhibit expression of a single class of immunoglobulin molecules (e.g., IgE molecules responsible for allergic responses) as opposed to all classes of immunoglobulins. Likewise, it may be necessary to target the coding sequence in order to inhibit expression of a gene containing a coding-sequence mismatch, mutation or other defect. In addition, sufficient and selective inhibition of translation using a blocking type mechanism may not be possible in all instances, even if the 5'-untranslated portion is targeted.

One approach to selective targeting of coding sequences is to rely on the ability of RNaseH to cleave duplexed RNA strands. In theory, by utilizing an anti-sense sequence which hybridizes to a target coding sequence on RNA, RNaseH cleavage of the target RNA could be achieved in this manner. However, in practice, cleavage by RNaseH requires that the strands in the target duplex sequence have 2'-deoxy sugar portions as well as charged (e.g., phosphodiester) backbone linkages. This means that uncharged-backbone anti-sense sequences such as methylphosphonate oligonucleosides (which are particularly useful because they are less subject to in vivo degradation) would not be expected to activate RNaseH activity against target RNA sequences. As a result, the increases in potency which can be achieved using modified oligonucleosides such as the methylphosphonates may not be realized (especially with respect to coding sequence targets) if RNaseH or translation arrest is relied upon to inhibit expression.

In an effort to increase the interference with protein synthesis of target genes and thereby increase potency, various agents can be bound to the anti-sense oligonucleotides which enhance the inactivation of the target nucleic acid. Such inactivating agents include alkylating agents, crosslinking agents and cleaving agents. These agents typically are capable of chemically modifying nucleic acid nonspecifically. By linking these agents to an anti-sense oligonucleotide, the target nucleic acid may in theory be modified or altered in specific locations.

Cleaving agents which have been covalently bound to oligonucleotides include, in particular, metal complexes such as EDTA-Fe(II), o-phenanthroline-Cu(II) and porphyrin-Fe(II). Uhlmann and Peyman, Antisense Oligonucleotides: A New Therapeutic Principle, *Chem. Rev.* 1990; 90:544–585. All of these cleaving agents require special conditions to perform the cleaving function. In each case, metal ion concentration must be carefully controlled to achieve cleavage. In some cases ancillary reagents not found in vivo such as peroxide, are required, making such agents inappropriate for in vivo use. Baker has also recently reported experiments using Cu(II)-phenanthroline and other metal ion complexes for attempted hydrolysis of 5'-capped mono- and oligoribonucleotides. Baker, B. F., *J. Am. Chem. Soc.,* 1993; 115:3378–3379.

Recently, a new class of non-site-specific nucleic acid cleaving agents has been investigated that do not require a metal ion free-radical mechanism to cleave the phosphodiester linkage. The design of these nucleic acid cleaving agents is intended to mimic the active site of naturally-occurring nucleases. Synthetic moieties modeled after nucleases such as staphylococcal nuclease have been reported to bind to phosphodiester linkages (Ariga & Ansilyn, *J. Org. Chem.* 1992; 57:417–419), as well as to accelerate both inter- and intramolecular phosphodiester cleavage Oubian, et al., *J. Am. Chem. Soc.* 1992; 114:1120–1121). In another example, staphylococcal nuclease has been coupled to a synthetic oligonucleotide in an effort to achieve site-specific cleavage activity. Corey & Schultz, *Science* 1987; 238:1401–1403. However, this approach suffers from problems of immunogenicity, instability in biological fluids, and poor cellular uptake. Oligoamines, such as ethylenediamine, triethylenetetramine and pentaethylenehexamine, have been reported to accelerate the hydrolysis of RNA. Yoshiari, et al., Oligoamines as Simple and Efficient Catalysts for RNA Hydrolysis, *J. Am. Chem. Soc.* 1991; 11 3:5899–5901.

SUMMARY OF THE INVENTION

The present invention relates to the inhibition of expression of a target nucleic acid by contacting the target nucleic acid, particularly mRNA, with an oligonucleoside compound and causing selective degradation (cleavage) of the target nucleic acid. The present oligonucleoside compounds, referred to herein as "cleavage compounds," are designed to target specific nucleic acid sequences by including an oligonucleoside sequence which is substantially complementary to a portion of the selected target nucleic acid, for example target mRNA. Such cleavage compounds maximize the rate of cleavage, including hydrolytic and/or transesterification cleavage, while retaining sequence specificity. Since selective cleavage of mRNA can prevent translation into encoded protein, the present compounds and methods prevent or reduce expression of the undesired protein encoded by the responsible gene. Such cleavage compounds may be expected to yield higher potencies than compounds associated with various other approaches to translation inhibition.

The present invention includes compounds which are structurally tailored so as to provide some or all of a number of cleavage-enhancing chemical functions. Specifically, certain of the present cleavage compounds are designed, in part, to mimic one or more of the chemical functions associated with RNA nucleases (RNases). Although the mechanism of RNA cleavage by RNases is not completely understood, it is believed that two histidine residues in the RNase active site synchronously deprotonate the 2'-OH and protonate the 5'-O of the target phosphodiester linkage, while orienting the deprotonated 2'-OH for nucleophilic attack on the phosphorus. Other compounds of the invention are believed to act primarily or even exclusively through a Lewis acid (electron-withdrawing) mechanism wherein the cleavage compound withdraws electrons from the target phosphorus-oxygen center, thereby facilitating direct nucleophilic attack by in situ water or hydroxide ion to effect hydrolytic cleavage.

More specifically, in one embodiment the present cleavage compounds are designed to promote cleavage, preferably in a site-specific fashion, by implementing or promoting several functions associated with enzymatic cleavage of RNA. These functions include (1) rotation of a target RNA sugar portion about the phosphodiester backbone of the target RNA, preferably to position a 2'-OH group of the target RNA for in-line, intramolecular attack on a neighboring phosphorus atom of the target backbone as achieved, for example, by incorporating an intercalating moiety, a base-omission mismatch, or some other non-complementary structure within the cleavage compound); (2) providing a nucleophilic moiety for attack on the target phosphorus atom, especially by deprotonation of the 2'—OH hydrogen of a target sugar on the target RNA (as achieved, for example, by increasing the local pH about the target sugar and/or by providing a basic or nucleophilic moiety in the vicinity of the target sugar); (3) supplying a proton or other electrophilic moiety for interaction with a phosphorus-bonded lone oxygen atom of the target RNA to form, for example, a protonated phosphate diester (as achieved, for example, by operation of an acidic or electrophilic moiety of the cleavage compound); (4) stabilizing the cleavage transition state, i.e., providing a structure on the cleavage compound to stabilize the intermediate structure or structures assumed by the target RNA during the cleavage mechanism, as by the inclusion of an acid-base moiety and/or other moieties which afford charge neutralization or hydrogen bonding stabilization to the intermediate (particularly polyfunctional groups capable of stabilizing a dianionic phosphorane in a trigonal bipyramidal configuration); and (5) providing a structure to protonate the leaving 5'-O oxygen atom of the target site, as by operation of an acidic moiety of the cleavage compound. Preferably, most or all of these functions are achieved by virtue of a single cleavage compound. Alternatively, such functions may be achieved by using in tandem two or more (but preferably two) cleavage compounds each of which provides some one or more of the individual functions identified above.

Additionally, or alternatively, the cleavage compounds may include a strong Lewis acid moiety, as for example a chelated metal species, which activates the phosphorus-oxygen center of a target phosphodiester bond (or of a target pyrophosphate linkage in the case of a 5'-cap region of a target RNA sequence) for direct hydrolytic cleavage by in situ water or hydroxide ion.

The cleavage compounds of the invention are preferably designed to form, in the course of cleavage, a hybridized duplex structure with a single-strand target RNA. However, the compounds may also be designed to form a triple-strand structure in the course of cleavage, as for example where two cleavage compounds act in tandem to form a triple-strand structure with a single-strand target RNA.

The cleavage compounds of the invention generally include a sequence of nucleosides that is chosen to be substantially complementary to a target region of the target nucleic acid strand, such that the cleavage compound is capable of hybridizing in a double-strand or triple-strand fashion to the target nucleic acid. In addition, the cleavage compounds each include one or both of (a) a portion that is "non-complementary" to the target strand and (b) a "cleavage moiety" portion.

The portion of the present cleavage compounds that is "substantially complementary" to the target RNA is chosen so as to provide suitable target specificity and binding affinity of the cleavage compound. Oligonucleosides of the present invention are preferably between about 6 to 40 nucleosides in length, more preferably between 12 to 30 nucleosides. The length of a particular cleavage compound, the number of complementary bases in the compound, and the identity and location of the complementary bases may be adapted so that suitable target specificity and binding affinity will be achieved under the conditions in which the compound will be used. These conditions include, for example, the effective concentration of the cleavage compound inside the cell, the concentration and turnover rate of the target sequence, the desired level of reduction of concentration of the target sequence, the efficacy of cleavage, and the mode of cleavage (e.g., catalytic or non-catalytic).

The "non-complementary" portion of a cleavage compound, if present, is selected so that Watson-Crick base pairing is eliminated or reduced between the non-complementary portion of the cleavage compound and one or more corresponding bases in the target region of the target nucleic acid. As such, the non-complementary portion of the cleavage compound assists in achieving the function of allowing rotation of a target RNA sugar portion about the sugar-phosphodiester "backbone" of the target RNA (function number (1) as listed above). Because the normal inter-strand hydrogen bonding forces are not present between the non-complementary portion of the cleavage compound and the corresponding base(s) on the target strand, the corresponding base(s) is not held within the inter-strand region and can "rotate" out from the inter-strand region. In turn, this allows or forces the sugar portion of the phosphodiester backbone of the target nucleic acid strand to assume a rotated conformation that enhances cleavage at or around the position of the rotated-out base. The non-complementary portion may comprise a non-nucleoside unit within the backbone of the cleavage compound (for example, a spacing or bridging portion optionally containing an intercalator or other steric or non-base-pairing group) that replaces a base-pairing unit to result in a "mismatch" with the corresponding base(s) of the target sequence, or it may simply comprise the omission of a base-pairing nucleoside unit from the sequence of the otherwise-complementary cleavage compound without replacement by an additional non-base-pairing unit. In the former case the non-complementary base on the target strand will rotate out according to a "loopout" motif as described hereinafter; in the latter case, the base will rotate out according to a "bulge-out" motif. The non-complementary portion may be situated internally within the nucleoside sequence of the cleavage compound, or it may be located at a terminus of the compound.

The "cleavage moiety" portion of the cleavage compound is a chemical group, or groups, that achieves two or more, and preferably most or all, of the functions numbered (2) through (5) above, or alternatively the Lewis acid function described above. Thus, in the former case, the cleavage moiety is preferably one which can act as both an acid (hydrogen-donor and/or electron-acceptor) and a base (hydrogen-acceptor and/or electron-donor). Polyamine groups may be particularly suited for this function. The basic activity of the cleavage moiety can act to increase the local pH about the target cleavage site and thereby stabilize nucleophile formation and facilitate nucleophilic attack, as by a deprotonated 2'-oxygen, on the backbone phosphorus of the target phosphodiester bond. The acidic hydrogen-donor activity of the cleavage moiety can act to facilitate protonation of the cleaved 5'-oxygen anion and/or to promote formation of a protonated phosphate diester as a cleavage intermediate. Preferably, the cleavage moiety will also contain groups which provide charge neutralization and/or hydrogen bonding so as to stabilize the formation of the trigonal bipyramidal transition state of the target phosphodiester bond, as for example by situating amine and/or ammonium groups near one or more oxygen atoms in the phosphodiester bond. Still further, the cleavage moiety may itself include a nucleophilic group suitable for attack on the phosphodiester bond, so as to achieve cleavage via a trans-esterification (rather than hydrolytic) reaction. Thus, such cleavage moieties will preferably comprise two or more distinct functional groups selected to provide two or more of the functions of proton donation, proton acceptance, hydrogen bonding and charge neutralization. Alternatively or additionally, Lewis acid (electron-acceptor) or electrophilic activity of the cleavage moiety, as for example with a chelated metal portion of the cleavage moiety, can act to withdraw electrons from the phosphorus-oxygen target site and thereby enhance nucleophilic attack by the 2'-OH oxygen or other nucleophilic (e.g., in situ water or hydroxide ion) species.

The cleavage moiety may be positioned as part of the non-complementary portion of the cleavage compound or it may be attached at a position separate from the non-complementary portion of the cleavage compound. For example, the cleavage moiety may be attached to a nonnucleoside, non-complementary bridging unit within the backbone of the compound, or it may be attached to a complementary nucleoside unit in the compound. Alternatively, the cleavage moiety may be situated on a separate cleavage compound that is used alone or in tandem with a first cleavage compound containing the non-complementary portion. Multiple cleavage moieties may be employed, whether on a single cleavage compound or on tandem cleavage compounds.

When a single cleavage compound is to be used to accomplish the intended cleavage (i.e., when the compound is not being used in tandem with another cleavage compound), then the cleavage compound will, in one embodiment, include both a non-complementary portion and a cleavage moiety portion, in addition to a nucleoside sequence that is substantially complementary to the target nucleic acid sequence. In an alternative embodiment, a single cleavage compound may be utilized without a specific non-complementary portion included therein, as for example in the case of a chelated metal cleavage moiety which acts to withdraw electrons from the phosphorus-oxygen target site so as to enhance direct hydrolytic cleavage via a water or hydroxide ion attack. If two different cleavage compounds are to be used in tandem to accomplish the intended cleavage, then it is possible to incorporate the non-complementary portion in one of the two tandem cleavage compounds, and the cleavage moiety in the other tandem cleavage compound. At least one, and preferably both, of the tandem cleavage compounds will incorporate a nucleoside sequence that is substantially complementary to the target nucleic acid sequence or a subregion thereof.

The present oligonucleoside cleavage compounds preferably are modified to render them resistant to degradation by cellular nucleases or other enzymes that are present in vivo. This modification can be accomplished by methods known in the art, e.g., by incorporating one or more internal artificial internucleoside linkages, such as by modifying the phosphodiester linkage to include alternate or additional groups in conjunction with a phosphorus atom (e.g., by replacing one of the non-bridging phosphate oxygens in the linkage with sulfur or other atoms), and/or by blocking the 3'end of the oligonucleoside with a capping structure. Likewise, the non-complementary and cleavage moiety portions can be conjugated to the cleavage compound using similar attachment chemistry, or using other techniques as described below.

Several advantages are provided by the cleavage compounds according to the present invention. The present compounds are target-mRNA-specific by virtue of their complementary oligonucleotide character, and therefore can be used against mRNA specific to a particular disease state. The present compounds are also capable of site-specific cleavage of the target RNA. In one preferred embodiment, the cleavage agents disclosed herein destabilize the RNA backbone by placing a 2'-OH of the target RNA in a nucleophilic attack position with respect to the 3'-adjacent phosphorous atom. Since DNA does not contain a 2'-OH, DNA should be generally unaffected by treatment with the present compounds. In another preferred embodiment in which the cleavage moiety is an active electron-withdrawing or Lewis acid species, the cleavage agents facilitate hydrolysis by enhancing attack by an in situ nucleophilic species (especially water or hydroxide ion) on a target phosphodiester bond, or on a target pyrophosphate bond in the 5'-cap region of a target RNA sequence. In either case, no free-radical mechanism utilizing metal ions or other compounds is required to implement the cleavage of the target RNA, making in vivo applications possible. Since the hydrolysis or transesterification cleavage is performed by nucleophilic attack, rather than by hydroxyl free-radical attack as is common with some metal ion complexes, only the desired cleavage site should be hydrolyzed by the present compounds. Further, eliminating the creation of free radicals by the cleaving agent also allows in vivo use, as the present compounds are expected to be relatively harmless to non-targeted nucleic acid. The present compounds in some instances may also be catalytic in nature, permitting the administration of a relatively small amount of the present compounds for treatment.

Another feature of the present invention is the administration of the cleavage compounds described herein to treat diseases or other conditions characterized by the presence of undesired nucleic acid. The methods of the present invention are useful for inhibiting the expression of protein encoding genes. Administration of the present cleavage compounds can be accomplished by methods known in the art, such as systemic, topical or localized administration. Preferably, the present cleavage compounds are administered in an amount sufficient to prevent or reduce the normal translation of the target nucleic acid.

Other features and advantages of the present invention will be apparent upon review of the detailed description of the preferred embodiment, the drawings and the claims.

BRIEF DESCRIPTION OF THE DRAWINGS

FIG. 1A) and 3'-5' RNA (Form B; FIG 1B).

DEFINITIONS

Figure 1A:
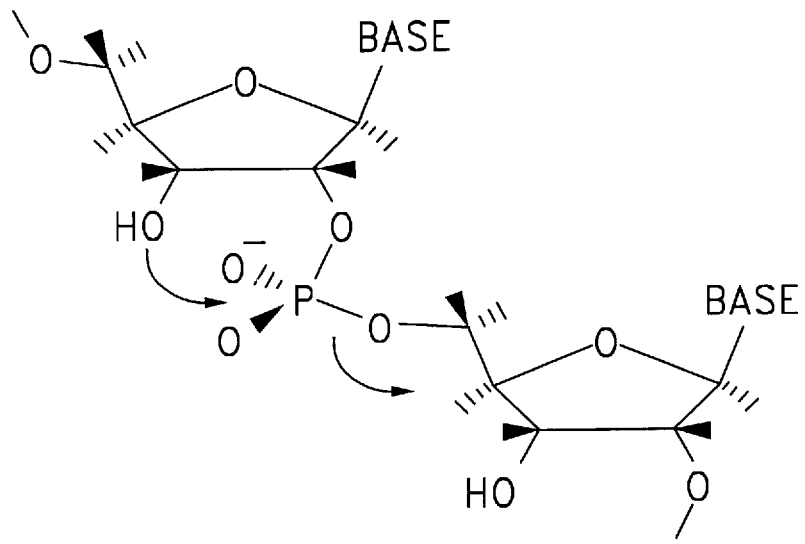
FIGS. 1A–1B is a representation of adjacent nucleotide units of 2'-5' RNA (Form A.

As used herein, the following terms have the following meanings unless otherwise indicated.

The term "nucleoside" includes a nucleosidyl unit and is used interchangeably therewith, and refers to a subunit of a nucleic acid which comprises a 5-carbon sugar and a nitrogen-containing base. The term includes not only those nucleosidyl units having A, G, C, T and U as their bases, but also analogs and modified forms of the naturally-occurring bases, including the pyrimidine-5-donor/acceptor bases such as pseudoisocytosine and pseudouracil and other modified bases (such as 8-substituted purines). In RNA, the 5-carbon sugar is ribose; in DNA, it is a 2'-deoxyribose. The term nucleoside also includes other analogs of such subunits, including those which have modified sugars such as 2'-O-alkyl ribose.

The term "nucleotide" refers to a subunit of a nucleic acid which consists of a nucleoside plus a phosphate group.

The term "purine" or "purine base" includes not only the naturally occurring adenine and guanine bases, but also modifications of those bases, such as bases substituted at the 8-position, or guanine analogs modified at the 6-position or the analog of adenine, 2-amino purine, as well as analogs of purines having carbon replacing nitrogen at the 9-position, such as the 9-deaza purine derivatives and other purine analogs.

The term "phosphonate" refers to the group

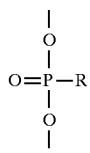

wherein R is hydrogen or an alkyl or aryl group. Suitable alkyl or aryl groups include those which do not sterically hinder the phosphonate linkage or interact with each other. The phosphonate group may exist in either an "R" or an "S" configuration. Phosphonate groups may be used as internucleosidyl phosphorous group linkages (or links) to connect nucleosidyl units.

The term "phosphodiester" or "diester" refers to the group

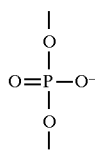

wherein such phosphodiester groups may be used as internucleosidyl group linkages (or links) to connect nucleosidyl units.

A "non-nucleoside unit" refers to a monomeric unit wherein the base, the sugar and/or the phosphate backbone or other internucleosidyl linkage group of a nucleoside has been replaced by some other chemical moiety(s).

A "nucleoside/non-nucleoside polymer" refers to a polymer comprised of nucleoside and non-nucleoside monomeric units.

The term "oligonucleoside" refers to a chain of nucleosides, optionally containing one or more non-nucleoside units, which are linked by internucleoside linkages. Such a chain is generally from about 4 to about 100 nucleosides in length, but which may be greater than about 100 nucleosides in length. It may be synthesized from nucleoside monomers or may also be obtained by enzymatic means. Thus, the term oligonucleoside refers to a chain of nucleosides which have internucleosidyl linkages linking the nucleoside monomers and, thus, includes oligonucleotides; nonionic alkyl- and aryl-phosphonate oligonucleotide analogs; alkyl- and aryl-phosphonothioate, phosphorothioate and phosphorodithioate oligonucleotide analogs; phosphoroamidate oligonucleotide analogs; neutral phosphate ester oligonucleotide analogs, such as phosphotriesters; and other analogs and modified forms of linked nucleosides, including nucleoside/non-nucleoside polymers. The term also includes linked nucleosides and nucleoside/non-nucleoside polymers wherein one or more of the phosphorus group linkages between monomeric units has been replaced by a non-phosphorus linkage such as a formacetal linkage, a thioformacetal linkage, a sulfamate linkage, or a carbamate linkage. The term also includes nucleoside/non-nucleoside polymers wherein both the sugar and the phosphorus moiety of one or more monomeric units have been replaced or modified such as with morpholino base analogs, or polyamide base analogs. The term also includes nucleoside/non-nucleoside polymers wherein the base, the sugar, and the phosphate backbone of one or more monomeric units are replaced by a non-nucleoside moiety or wherein a non-nucleoside moiety is inserted into the nucleoside/non-nucleoside polymer. Optionally, said non-nucleoside moiety may serve to link other small molecules which may interact with target sequences or alter uptake into target cells. The term also includes nucleoside/non-nucleoside polymers wherein a non-complementary portion and/or a cleavage moiety portion, as described herein, are inserted into the polymer.

The term "alkyl- or aryl-phosphonate oligonucleoside" refers to oligonucleosides having at least one alkyl- or aryl-phosphonate internucleosidyl linkage. Suitable alkyl- or aryl-phosphonate groups include alkyl- or aryl- groups which do not sterically hinder the phosphonate linkage or interact with each other. Preferred alkyl groups include lower alkyl groups having 1 to about 6 carbon atoms. Suitable aryl groups have at least one ring having a conjugated pi electron system and include carbocyclic aryl and heterocyclic aryl groups, which may be optionally substituted and preferably having up to about 10 carbon atoms.

The term "methylphosphonate oligonucleoside" refers to oligonucleosides having at least one methylphosphonate internucleosidyl linkage.

The term "neutral oligonucleoside" refers to oligonucleosides which have nonionic internucleosidyl linkages between nucleoside monomers (i.e., linkages having no positive or negative ionic charge) and include, for example, oligonucleosides having internucleosidyl linkages such as alkyl- or aryl- phosphonate linkages; alkyl- or aryl-phosphonothioate linkages; neutral phosphate ester linkages such as phosphotriester linkages, especially neutral ethyltriester linkages; and neutral non-phosphorus containing internucleosidyl linkages, such as sulfamate, morpholino, formacetal, thioformacetal, and carbamate linkages. Optionally, a neutral oligonucleoside may comprise a conjugate between an oligonucleoside (including a nucleoside/non-nucleoside polymer) and a second molecule which comprises a conjugation partner. Such conjugation partners may comprise intercalators, alkylating agents, binding substances for cell surface receptors, lipophilic agents, nucleic acid modifying groups including photo-cross-linking agents such as psoralen and groups capable of cleaving a targeted portion of a nucleic acid, and the like. Such conjugation partners may further enhance the uptake of the oligonucleoside, modify the interaction or the oligonucleoside with the target sequence, or alter the pharmacokinetic distribution of the oligonucleoside. The essential requirement is that the oligonucleoside comprised by the oligonucleoside conjugate be substantially neutral.

The term "substantially neutral" in referring to an oligonucleoside refers to those oligonucleosides in which at least about 80 percent of the internucleosidyl linkages between the nucleoside monomers are nonionic linkages.

The term "neutral alkyl- or aryl- phosphonate oligonucleoside" refers to neutral oligonucleosides having neutral internucleosidyl linkages which comprise at least one alkyl- or aryl- phosphonate linkage.

The term "neutral methylphosphonate oligonucleoside" refers to neutral oligonucleosides having internucleosidyl linkages which comprise at least one methylphosphonate linkage.

The term "complementary" refers to oligonucleosides (or nucleoside units therein), especially anti-sense sequences, having a nucleoside sequence (or a base portion) which is capable of forming hydrogen bonds, and thereby base pairing or hybridizing, with the base sequence of a region of the target nucleic acid to form a Watson-Crick or "double helix" type structure (whether or not actually helicized) or a portion thereof.

The term "substantially complementary" refers to oligonucleosides which may lack a complement for one or more nucleotides in the target region or subregion, but which still have sufficient binding affinity for the target sequence to form a hybridized, double helix type structure within the subject (e.g., in vivo) environment, so as to specifically recognize the target sequence and promote cleavage as described herein. The term also embraces oligonucleosides, or pairs of distinct oligonucleosides which have sufficient complementarity to achieve triple-strand binding with a target nucleic acid single-strand sequence in the subject environment, thereby to promote cleavage as described herein.

DETAILED DESCRIPTION OF THE PREFERRED EMBODIMENT

According to the present invention, methods and compounds for inhibiting the undesired expression of genes are described. Specifically, strategies are described for preparing oligonucleoside cleavage compounds that are specific to a target region or subregion of the target nucleic acid sequence and contain non-complementary and/or cleavage moiety portions which facilitate the hydrolysis or other cleavage of the target nucleic acid. Also described are preferred methods for administering oligonucleoside cleavage compounds prepared according to the present invention to treat diseases or conditions associated with the undesired expression of a target nucleic acid.

More particularly, the invention includes oligonucleoside compounds for hybridizing to a target nucleic acid strand, comprising an oligonucleoside sequence that is substantially complementary to a target region or subregion of the target nucleic acid strand, and a portion that is non-complementary to a site in the target region or subregion such that, when the oligonucleoside compound is hybridized to the target strand, a base group at said site is oriented away from an inter-strand orientation. The non-complementary portion may be internal to the oligonucleoside sequence, or it may be positioned at a terminus of the sequence. The non-complementary portion may include a steric group such as an intercalator group. Such compounds may further include a cleavage moiety, the cleavage moiety comprising one or more functional groups selected from proton donors, proton acceptors, hydrogen bonding groups, charge neutralizing groups and Lewis acids, said groups being selected to enhance cleavage in the target region of the target nucleic acid strand at the site at which the base group is oriented away from an inter-strand orientation. Preferably, the cleavage moiety comprises two or more distinct functional groups selected to provide two or more of the functions of proton donation, proton acceptance, hydrogen bonding and charge neutralization. Among these are cleavage moieties comprising two or more amino groups, and wherein at least one amino group is substantially protonated, and at least one amino group is substantially nonprotonated, at physiological pH. Also preferred are cleavage moieties comprising a Lewis acid consisting of a complexed (e.g. chelated) metal ion. The cleavage moiety may be linked to the non-complementary portion of the oligonucleoside cleavage compound, or it may be linked at a position separate from the non-complementary portion.

As described hereinafter, the invention further includes combinations of two (or more) oligonucleoside cleavage compounds for use in tandem with one another, wherein a first such tandem compound, or the tandem compounds together upon hybridization, comprise a non-complementary portion as described herein, and a second such tandem compound comprises a cleavage moiety as described herein. In one embodiment, each compound of the combination independently comprises a targeting subportion sequence of nucleosides that is substantially complementary to a target subregion of the target nucleic acid strand that is proximate to (neighbors) or is adjacent to the target subregion of the other oligonucleoside cleavage compound. Such tandem cleavage compounds may further include, respectively, first and second mating subportions for hybridizing to one another and having nucleoside sequences that are substantially complementary to one another (and not substantially complementary to the target strand). Alternatively, the two tandem cleavage compounds may include first and second mating subportions as described above, and one or the other of the two tandem cleavage compounds may then further include an oligonucleoside sequence that is substantially complementary to a target region or subregion of the target nucleic acid strand. Still further, three tandem cleavage compounds may include first, second and third mating subportions for triple-strand hybridization with one another, and two of the compounds may then further include first and second targeting subportions that are substantially complementary to neighboring or adjacent subregions of the target strand. When such tandem cleavage compounds are hybridized to the target strand and/or to one another, the non-complementary portion or structure and the cleavage moiety on the hybridized tandem compounds are situated so as to be proximate to one another, and to a target site in the target nucleic acid strand, so as to effect cleavage at the target site.

Alternatively, multiple tandem cleavage compounds may be used in combination wherein each compound has substantial triple-strand complementarity to a target region of the target nucleic acid strand, the first tandem compound having a non- complementary portion and the second tandem compound having a cleavage moiety, as described herein.

The invention further includes oligonucleoside cleavage compounds for hybridizing to the 5'-terminal region of a target mRNA nucleic acid strand and effecting cleavage thereof, comprising an oligonucleoside sequence that is substantially complementary to the 5'-terminal region of the target nucleic acid strand, and a cleavage moiety situated at a position in the cleavage compound that is proximate to the 5'-cap structure of the target strand upon hybridization, such that the cleavage moiety is capable of effecting cleavage of the 5'-cap structure of the target strand.

The present invention also provides methods for inhibiting production of a selected protein (or peptide) in a cell or by a multicellular organism (such as a mammal), comprising administering to the cell or organism a cleavage compound, or a combination of cleavage compounds, as described herein in an amount effective to effect cleavage at a site in a target region of the RNA that codes for the selected protein. Conditions caused by the production of the selected protein or peptide may thereby be therapeutically treated, or the effects of such cleavage and inhibition may be studied in in vitro or ex vivo environments.

As will be seen, certain of the oligonucleoside cleavage compounds of the invention are effective in combination with one another to achieve cleavage of a target nucleic acid strand. Other cleavage compounds are effective individually to achieve cleavage. In each case, the oligonucleoside sequence of the compounds will be chosen so as to target a desired region of a selected nucleic acid strand, and to provide a cleavage moiety and, upon eventual hybridization with the target strand, a portion or structure that is non-complementary to the sequence of the selected target strand. However, while the structure of a given cleavage compound will be chosen to achieve eventual hybridization and cleavage of the selected target strand, it will be appreciated that the present invention includes the described oligonucleoside cleavage compounds themselves, and combinations thereof, separate from the selected nucleic acid strand that is ultimately to be targeted and cleaved.

A. Preferred Complementary Oligonucleoside Structures

The therapeutic approach and the cleavage compounds of the present invention are based on the principle that the function of a gene can be disrupted by preventing or inhibiting expression of the protein or other product encoded by that gene. In principle, protein synthesis disruption can be accomplished by providing an oligonucleoside of appropriate structure and length which is complementary to at least a portion of the messenger RNA (mRNA) transcribed from the target gene. Such complementary sequences are commonly called "anti-sense" compounds. In the present invention, the anti-sense oligonucleoside cleavage compound hybridizes in the intracellular environment with the target mRNA and inactivates the mRNA by cleaving the target strand, thereby preventing ribosomal translation and resultant protein synthesis.

The oligonucleoside cleavage compounds of the invention will typically have a sequence that is complementary to a target region or subregion of the sequence of the target nucleic acid. (As discussed below, a "tandem" cleavage compound may additionally, or alternatively, include a mating portion that is complementary to the other tandem cleavage compound of the tandem pair.) However, absolute base-by-base complementarity is not normally required. Any oligonucleoside having sufficient complementarity to form a stable and target-specific duplex or triplex hybrid with the target nucleic acid in the subject environment, and thereby being capable of effecting cleavage, is "substantially complementary" and is considered to be suitable.

Efficacy of hybridization is related to the strength of the hydrogen bonding between corresponding bases as well as the specificity of the cleavage compound to the complementary target nucleic acid. The specificity of anti-sense oligonucleosides arises from the formation of Watson-Crick base pairing between the heterocyclic bases of the oligonucleoside and spatially-proximate complementary bases on the target nucleic acid. The strength of the hydrogen bonding is influenced by the number and percentage of bases in an anti-sense olignucleoside cleavage compound that are base-paired to complementary bases on the target sequence, according to Watson-Crick base pairing. To be specific for the target nucleic acid strand, the complementary bases of the anti-sense cleavage compound must be sufficient in number as to avoid non-specific binding to other non-target sequences within the mRNA population, and at the same time small enough in number to avoid non-specific binding between a subportion of the olignucleoside cleavage compound and non-target sequences.

For example, based on statistical considerations alone, a given nucleotide sequence 12 nucleotides in length will be expected to occur randomly only once every $4^{12}$, or about $2 \times 10^7$, nucleotides. Accordingly, such a 12-nucleotide sequence is expected to occur only once among the population of mRNA molecules transcribed by the human genome. In contrast, a nucleotide sequence 6 nucleotides in length might occur randomly every $4^6$, or 4096, nucleotides. Such a sequence might be present thousands of times among the population of transcribed RNA molecules in humans. Consequently, and within the limitations expressed above, complementary oligonucleosides of greater length (and having a defined sequence) are generally more specific than oligonucleosides of lesser length and are generally less likely to induce toxic complications that might result from unwanted hybridization and cleavage.

However, other factors will also influence the choice of oligonucleoside length that is optimum for a given cleavage application. These factors include the binding affinity of the cleavage compound for the particular target nucleic acid sequence, which will influence the stability and lifetime of the hybrid structure, and in turn the kinetics of cleavage; the concentration of cleavage compound that can safely and practically be achieved inside the cell, given considerations such as the cellular uptake rate, the degradation rate and the clearance rate for the cleavage compound; the concentration and turnover rate of the target nucleic acid sequence, and the influence of various biological processes such as the processional rate of the ribosome along the mRNA-target; the level of reduction of concentration of the target sequence that is sought to be achieved; the efficacy and mode of cleavage (e.g., catalytic or non-catalytic); and other related factors.

Given the teachings of the present disclosure, those skilled in the art will be able to ascertain optimum oligonucleoside lengths, and suitable complementary sequences, to achieve structures that are substantially complementary to the desired target sequences and that have suitable potency. In general, oligonucleosides of about 6 to about 40 nucleosidyl units in length which have sufficient complementarity to form a double helix type structure having a melting temperature ($T_m$) of greater than about 40° C. under physiological conditions are particularly suitable for use according to the methods of the present invention. Preferably, the cleavage compounds of the invention each comprise from about 12 to about 30 nucleosides.

In one embodiment of the invention, tandem cleavage compounds are employed to effect cleavage of a single target nucleic acid sequence. In this instance, at least one (and preferably both) of the cleavage compounds of the tandem pair will include a portion that is substantially complementary to a subregion of the target nucleic acid sequence. Preferred tandem cleavage compounds include those which individually contain a total of about 6 to about 40 nucleosides, and preferably about 12 to about 30 nucleosides. Either or both of the tandem cleavage compounds in a tandem pair may include a cleavage moiety as described hereinafter. In addition, either or both of the tandem cleavage compounds may include a non-complementary portion, or the tandem compounds may jointly form a non-complementary structure when they are hybridized to one another.

The complementary oligonucleoside sequence of the present cleavage compounds may be selected based on analysis of the sequence of the gene to be inhibited, by analysis of mRNA transcribed from that gene (as by analysis of cDNA reversed transcribed from such mRNA), by analysis of the amino acid sequence of the translated polypeptide product, or by other methods. The gene sequence can be determined, for example, by isolation and sequencing, or if known, through the literature.

The oligonucleoside selected may be any of a number of types, including those having charged or uncharged internucleosidyl bonding groups in the "backbone" of the sequence. Preferred oligonucleosides include alkyl- or aryl-phosphonates with methylphosphonates being especially preferred. Other preferred oligonucleosides include phosphorothioates, morpholino analogs, formacetal analogs and peptide nucleic acid ("PNA") analogs, and mixtures of such analogs in a single oligonucleoside compound.

Oligonucleosides having the desired internucleoside linkages may be conveniently prepared according to synthetic techniques known to those skilled in the art. For example, commercial machines, reagents and protocols are available for the synthesis of oligonucleosides having phosphodiester and certain other phosphorus-containing internucleoside linkages. See also Gait, M. J., *Oligonucleotide Synthesis: A Practical Approach* (IRL Press, 1984); Cohen, Jack S., *Oligodeoxynucleotides Anti-sense Inhibitors of Gene Expression* (CRC Press, Boca Raton, Fla., 1989); and *Oligonucleotides and Analogues: A Practical Approach*, (F. Eckstein, 1991); Agrawal, S. (ed.), *Protocols for Oligonucleosides and Analogs, Methods in Molecular Biology*, Vol. 20 (Humana Press, Totowa N.J. 1993).

Preparation of oligonucleosides having certain non-phosphorus-containing internucleotide linkages is described in U.S. Pat. No. 5,142,047, the disclosure of which is incorporated herein by reference. More particularly, synthetic methods for preparing methylphosphonate oligonucleosides are described in Agrawal, above, Chapter 7, pages 143–164 (Hogrefe, R. I.), and in commonly-assigned published PCT applications WO 92/07864 and WO 92/07882, the disclosures of which are incorporated herein by reference. Particular methods for preparing representative oligonucleosides for cleavage purposes are described in examples given below.

Other functional groups may also be joined to the oligonucleoside sequence to instill a variety of desirable properties, such as to enhance uptake of the oligonucleoside sequence through cellular membranes, to enhance stability or to enhance the formation of hybrids with the target nucleic acid, or to promote cross-linking with the target. See, for example, copending U.S. patent application Ser. No. 08/068,140 and WO 92/02532.

In one preferred aspect of the invention, chirally pure oligonucleosides are used. Alternatively, oligonucleosides comprising at least one chirally pure internucleosidyl linkage may be used and may be preferred. Such oligonucleosides, for example with methylphosphonate or phosphorothioate linkages, may be prepared using methods as those described in Lesnikowski, et al., *Nucleic Acids Research* 1990; 18(8):2109–2115 and Stec, et al., *Nucleic Acids Research* 1991; 19(21):5883–5888. Preferably, the methods described in commonly-assigned copending U.S. patent application Ser. Nos. 08/154,013 and 08/154,014 may be employed.

Suitable oligonucleosides also include chimeric oligonucleotides which are mixed RNA, DNA analogs (Perreault, et al., *Nature* 1990; 344:565–567). Other suitable oligonucleosides include those having chimeric backbones. Such backbones may include a mixture of internucleosidyl linkages which may or may not include phosphorus atoms, such as morpholinyl linkages, formacetal linkages, peptide nucleic acid (PNA) linkages and the like. Oligonucleosides having a neutral backbone, for example methylphosphonate oligonucleosides may have a longer half-life in vivo since the neutral structure reduces the rate of nuclease digestion.

B. Non-Complementary Portions of the Cleavage Compounds

In one embodiment, the cleavage compounds of the present invention contain at least one non-complementary portion. The non-complementary portion is chosen such that, when the cleavage compound is hybridized to the target nucleic acid, the non-complementary portion does not provide the normal Watson-Crick hydrogen bonding with the corresponding base group (or groups) on the target strand. Thus, unlike the other base-paired (i.e., complementary) bases in the hybrid, the non-base-paired (i.e., non-complementary) target site base on the target strand is not held in the inter-strand region, and will be free to orient itself away from an inter-strand orientation. This re-orientation or "rotating out" of the non-complementary target site base on the target strand in turn causes the associated sugar on the non-complementary nucleotide unit to rotate with respect to the target phosphodiester backbone and assume a position that enhances internucleotidyl bond cleavage. The rotating-out effect may be enhanced by including a space-filling, non-hydrogen bonding group (e.g., an intercalator) in the non-complementary portion, or it may be achieved by a simple "mismatch," that is, the absence of a hydrogen bonding group in the non-complementary portion. Alternatively, the non-complementary portion may be formed by omitting one (or more) complementary nucleosides within an oligonucleoside sequence that is otherwise complementary to the target nucleic acid sequence. Further, the non-complementary portion may be a structure formed by two (or more) tandem cleavage compounds which hybridize via mating portions to one another, as in the case of a "three-way junction" structure as described hereinafter.

Certain of the cleavage principles of the present invention may be better understood by considering the structural differences between 2'-5' and 3'-5' phosphodiester RNA polymers. It is known that 2'-5' phosphodiester polymers of ribonucleic acids are less stable against hydrolysis than helicized forms of the naturally occurring 3'-5' phosphodiester linkage. Usher and McHale, *Proc. Natl. Acad. Sci. U.S.A.* 1976; 73:1149–1153. The nucleotide bases in helical (particularly multi-stranded) RNA polymers, and in some (particularly purine-rich) single-stranded RNA polymers, tend to orient by inter-strand forces or stacking interactions. As a result, the nonesterified 3'-OH hydroxyl moieties on the sugar groups of 2'-5' RNA polymers tend to be in a favorable conformation with respect to a hydrolytic reaction mechanism of internucleoside cleavage. In contrast, the nonesterified 2'-OH of 3'-5' RNA is in an unfavorable conformation for hydrolysis.

Figure 1B:
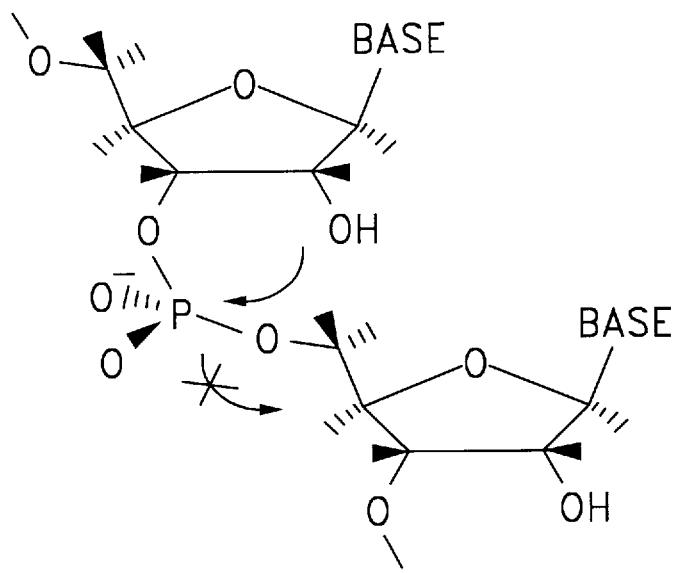

The intramolecular cleavage reaction in the case of 2'-5' RNA is thought to proceed via a trigonal-bipyramidal reaction intermediate, in which the displaced 5'-OH and the attacking 3' nucleophilic oxygen are oriented opposite one another at the apices of the bipyramidal structure. Thus, as seen in FIGS. 1A–1B, the 3'-OH is available for a direct in-line displacement reaction in 2'-5' RNA (Form A; FIG. 1A), whereas the 2'-OH in 3'-5' RNA (Form B; FIG. 1B) tends to be in a conformation which is unavailable for in-line displacement. In fact, Usher and McHale found that 2'-5' RNA is 900 times more susceptible (based on initial reaction rate) to hydrolysis compared to 3'-5' RNA. This increased susceptibility to hydrolysis is said to be due to the more favorable orientation of 2'-5' RNA for direct, apical nucleophilic attack by the 3'-OH on the phosphorus and immediate in-line displacement of the opposing apically-positioned 5'-oxygen of the adjacent nucleotide.

Based upon the results of 3'-5' RNA hydrolysis studies by the present inventors which are described in detail in Example 2 below, a RNA strand is much more slowly hydrolyzed by ethylenediamine when a complementary (e.g. methylphosphonate) oligo-nucleoside is permitted to hybridize with the target RNA, compared to the same RNA strand in the absence of a complementary oligonucleoside. This result is believed to be due to the fact that the 2'-OH moieties of the target RNA strand are held in a non-preferred conformation for nucleophilic displacement when the target mRNA bases are oriented in a double-helix configuration by hydrogen bonding to the complementary oligonucleoside. Conversely, as shown in Examples 3 and 6, the rate of site-specific cleavage is increased upon exposure of a target RNA sequence to a cleavage compound containing a non-complementary portion (Example 3) and additionally a cleavage moiety portion (Example 6) according to the present invention. These results indicate that, in the heteroduplex, the non-complementary portion causes the corresponding target RNA base to rotate or orient itself away from an inter-strand orientation, and the target nucleotide to assume a conformation that is preferred for cleavage. In contrast, the target nucleotide less often assumes this conformation in single-stranded RNA alone, particularly in helicized or heteroduplex RNA.

complementary portion may comprise a non-nucleoside or other non-hydrogen bonding group within the backbone of the compound that bridges two subportions of the cleavage compound that are themselves complementary to two non-adjacent subregions of the target region of the target nucleic acid sequence. (These subregions of the target sequence, while proximate to or neighboring one another, are "non-adjacent" because at least one non-complementary nucleotide in the target strand-viz., the nucleotide that is opposite the non-complementary portion of the hybridized cleavage compound-separates the complementary subregions.) One depiction of a cleavage compound of the invention having such an internally-located non-complementary bridging portion is as follows:

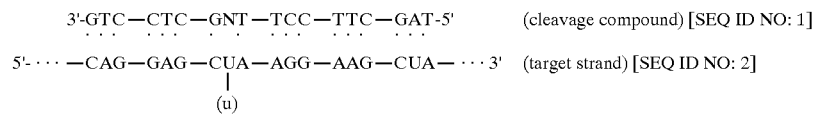

In order to help overcome the relative stability against hydrolysis of the 3'-5' phosphodiester configuration of naturally-occurring mRNA, the present invention in one embodiment utilizes a chemical structure, referred to here as a non-complementary portion, which is capable of selectively altering the natural steric conformation of the target RNA so as to promote hydrolytic or transesterification cleavage of the target phosphodiester bond or bonds. In this regard, it will be noted that the stability of 3'-5' RNA against hydrolysis increases as the RNA strand achieves a helical conformation (see discussion above); thus, the use of an anti-sense oligonucleoside in the absence of such other features as are taught herein would be expected to decrease the susceptibility of the target mRNA to cleavage. In contrast, one significant and surprising aspect of the present invention is that the inclusion of a non-complementary portion in an otherwise complementary oligonucleoside structure is useful in selectively rotating a base in the target RNA strand away from an inter-strand orientation to achieve a conformation in which the 2'-OH of the RNA favors an in-line displacement reaction.

Figure 2A:
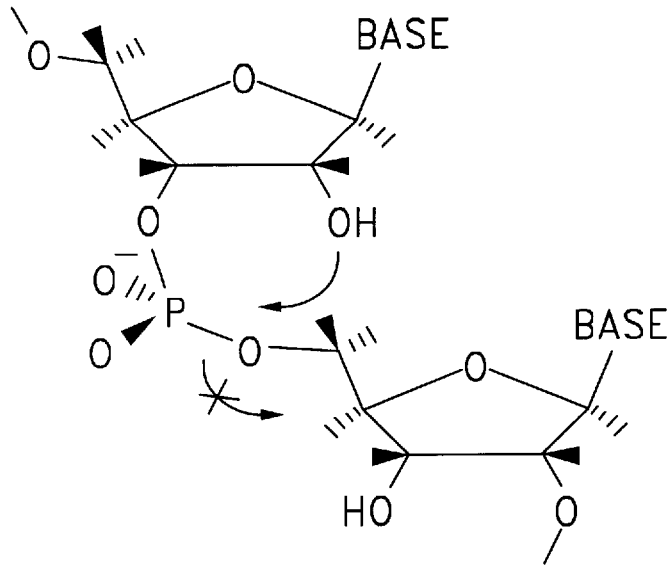
FIGS. 2A–2B is a representation of a 3'-5' RNA portion in its normal configuration (left) and a in a rotated configuration (FIG. 2B) in which a sugar-base portion has been rotated 180° about the 3'-oxygen/phosphorus bond.
Figure 2B:
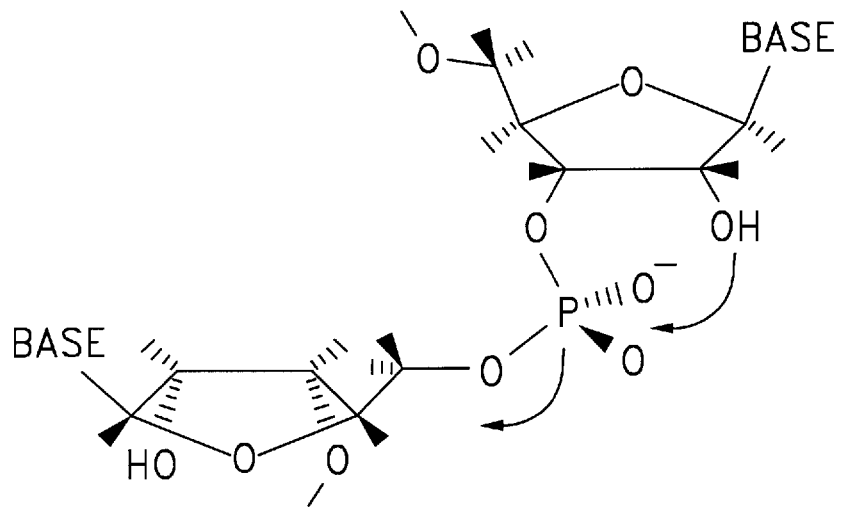

The non-complementary portion should allow rotation of the target RNA backbone up to 180° to approximate the conformation shown FIG. 2B. Here, it can be seen that the 2'-OH of the upper nucleotide is in position for an apical, in-line attack on the phosphorus. In contrast, the 2'-OH is not in position for such attack in the non-rotated structure (FIG. 2A). Most preferably, the nucleotide on the target strand that is targeted for rotation will be one with a pyrimidine base, since these bases are less hydrophobic than purine bases and will more readily assume a rotated conformation in the cellular environment.

The non-complementary portion of a cleavage compound may be located internally within the overall oligonucleoside sequence of the cleavage compound, or it may be located at a terminal position. When located internally, the non- In this structure, the cleavage compound (top) contains an internal, non-complementary bridging portion (N) which does not provide hydrogen bonding to the uracil base (u) of the internal uridine nucleotide of the target strand (bottom). As a result of this mismatch, the uracil target site base is rotated or "looped" out from its normal inter-strand orientation, so as to place the sugar-phosphodiester backbone of the target strand into a conformation that facilitates cleavage of the uridine phosphodiester linkage. It will be understood that cleavage may be effected at either or both of the 3'- and 5'-phosphodiester bonds of the target uridine nucleotide (depending on the position at which the cleavage moiety is oriented for attack), because both such bonds are oriented for in-line displacement when the uracil base assumes its rotated conformation. It will also be understood that the particular nucleosides depicted for the cleavage compound and the target strand have been chosen arbitrarily above for purposes of illustrating this principle of the invention, and that the nucleoside sequence of the present cleavage compounds will, in actual practice, be chosen to achieve hybridization with the desired target region of the target strand that is to be cleaved, as discussed above.

Examples 3 and 9 below describe the use of one such cleavage compound in enhancing the cleavage of a target strand in the presence of various separate cleavage moiety reagents. Examples 4–6 show the preparation of such compounds further including attached cleavage moieties and their use in cleaving a target strand.

In another form of an internal non-complementary portion, rotation of a target site base may be achieved by simply omitting one complementary nucleoside (or more) within the sequence of an otherwise-complementary oligonucleoside cleavage compound, without inserting any additional non-complementary bridging group, or only a very small group, between the complementary subportions of the compound. This may be depicted as follows:

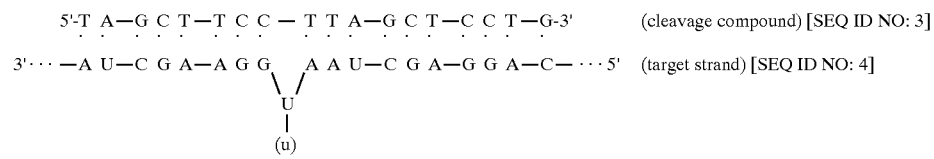

In this structure, the internal uridine nucleotide of the target strand (lower) is "bulged" out from the rest of the hybridized heteroduplex structure, and the 3'- and 5'- adjacent subregions of the target strand are drawn relatively closer together, because a complementary nucleoside has been omitted from the otherwise-complementary cleavage compound sequence (upper). In addition, the non-adjacent guanine and adenine bases situated on either side of the central uridine nucleotide in the target strand are capable of hydrogen bonding with the adjacently-situated cytosine and thymidine nucleosides of the cleavage compound. As a result of this "bulging" out, the uracil base of the uridine is rotated away from an inter-strand orientation, and the sugar-phosphodiester backbone of the target strand again assumes a conformation that facilitates cleavage of the uridine phosphodiester linkage.

Example 7 below describes the preparation of a cleavage compound using this bulge-out motif, and additionally the attachment of a cleavage moiety to one of the complementary bases of the cleavage compound.

As discussed in more detail below, the non-complementary portion of a cleavage compound may alternatively be situated at a terminus of the cleavage compound. Such positioning is particularly suited for use with tandem cleavage compounds, as for example where a cleavage moiety is situated at the "abutting" terminus of the second cleavage compound of the tandem pair. This approach may be depicted as follows, wherein "N" represents a non-complementary portion on a terminus of a first tandem cleavage compound, and "C—*" represents a complementary nucleoside on a terminus of a second cleavage compound (for example, a modified cytosine base) or other group which bears a cleavage moiety:

In this case, cleavage may be effected at two separate sites in the target strand, by operation of the two cleavage moieties in the middle tandem cleavage compound, facilitated by the two non-complementary portions at or near the respective abutting termini of the two laterally-hybridized tandem cleavage compounds. It will be understood that the lengths of the compounds shown above are arbitrary for purposes of illustration, and that longer tandem compounds may generally be used in actual practice. Further, it will be understood that the two cleavage moieties need not be situated on the same tandem compound, and may be situated, for example, on one or both of the two laterally-hybridized tandem compounds. Likewise, one or more of the non-complementary portions may be situated in the middle tandem compound.

The non-complementary portion of a cleavage compound may consist exclusively of a bridging portion or an omitted nucleoside without additional structural groups, or it may further include structures which are chosen to enhance (a) the rotation of a target nucleotide base and/or (b) the bond-breaking mechanism itself. Thus, in the latter case, a cleavage moiety (as described in more detail below) may be directly conjugated to the non-complementary portion of the cleavage compound.

In order to facilitate the base rotation function, a functional group of substantial steric size may be additionally incorporated as part of the non-complementary portion in order to actively force the target base away from the inter-strand region. Non-nucleoside groups such as interca-

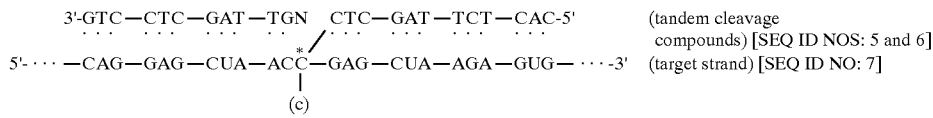

(tandem cleavage compounds) [SEQ ID NOS: 5 and 6]
(target strand) [SEQ ID NO: 7]

As discussed hereafter, the cleavage moiety (*) is attached to the right-most tandem cleavage compound at or near its 3'-terminal nucleoside, using a linker arm or other attachment group that positions the cleavage moiety proximate to the target guanosine nucleotide so as to effect cleavage of a phosphodiester bond associated with the rotated guanosine sugar-base structure. (As elsewhere in this specification, the particular nucleosides illustrated are for purposes of example only and do not limit the present invention).

More than two tandem cleavage compounds, as discussed in more detail below, may also be used in the practice of the invention. By way of example, three such tandem compounds may be depicted as follows:

lating agents are especially preferred for this purpose. Thus, an intercalator group such as an acridinium adduct may be conjugated to the backbone structure of the non-complementary portion (whether internally- or terminally situated) so as to occupy the inter-strand region of the final hybridized structure without providing Watson-Crick hydrogen bonding to the corresponding base of the target mRNA. This not only allows the target base to escape stacking or other inter-strand orientational forces, but also employs steric effects to actively "loop" the non-complementary target base out of the inter-strand region. This may be depicted schematically as follows:

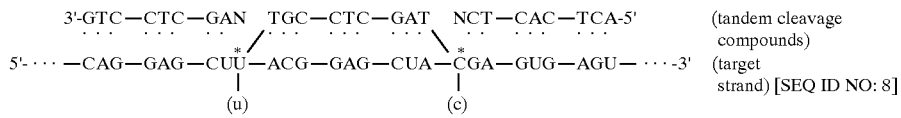

(tandem cleavage compounds)
(target strand) [SEQ ID NO: 8]

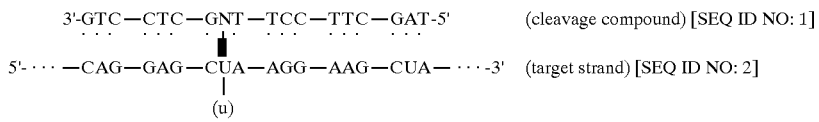

(cleavage compound) [SEQ ID NO: 1]

(target strand) [SEQ ID NO: 2]

Figure 3:
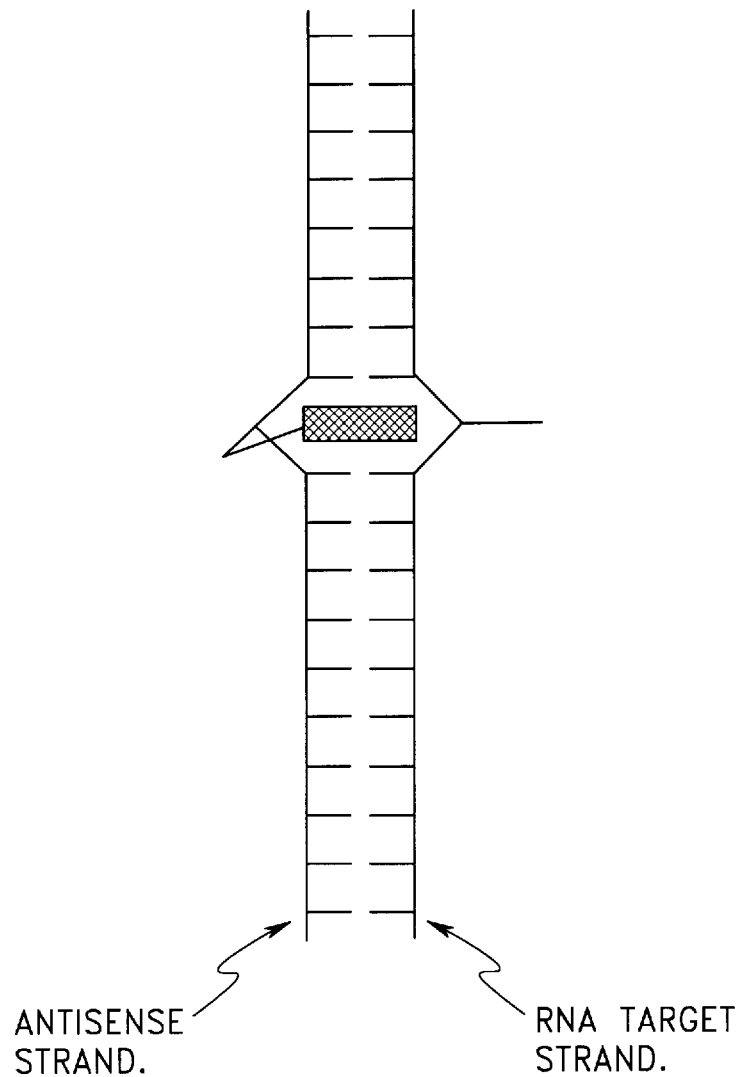
FIG. 3 is a schematic representation of an intercalating agent or other steric group on an anti-sense strand (left) which has caused a selected nucleotide on a target strand (right) to rotate out of its normal double-helix conformation.

Here, the structure ▮ represents a steric group, such as an intercalating agent, coupled to the non-complementary portion (e.g., backbone bridging group) of the cleavage compound. FIG. 3 shows another schematic depiction of such a compound of the invention.

As will be understood from the discussion herein, a cleavage moiety may also be attached to such a cleavage compound to enhance cleavage at the target site. This moiety may be linked to the steric group itself, or it may be linked directly to the cleavage compound backbone or to a complementary nucleoside base in the compound at a position that is proximate to the non-complementary portion. Such structures may be exemplified as follows:

Multiple, proximately-positioned cleavage moiety structures similar to those depicted above may also be used in a single (non-tandem) cleavage compound. The multiple cleavage moieties may be attached internally within the nucleoside sequence of the compound, or at or near a terminus of the compound.

Although non-complementary portions can be prepared and incorporated into the present compounds using many methods, the technology of commonly-assigned PCT Publication No. WO92/02532 is preferred. Thus, in the case of

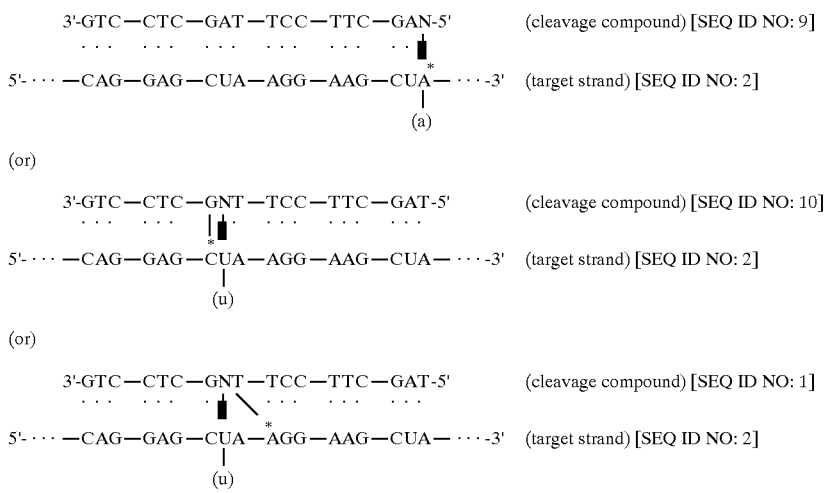

In the upper example, the cleavage moiety (*) is linked to the steric group which is at a terminal position in the cleavage compound. (Of course, such a linkage may also be used with an internally-situated non-complementary portion.) In the middle example, the cleavage moiety is linked to, for example, a modified guanine base in the cleavage compound, and is thereby positioned proximate to the 5'-internucleotidyl bond of the target uridine. In the lower example, the cleavage moiety is linked to, for example, the backbone bridging portion of the non-complementary portion (to which also is separately attached the steric group) so as to attack the 3'-internucleotidyl bond of the target uridine. It will also be understood that such structures may be used with tandem cleavage compounds, as for example where multiple cleavage moieties are used synergistically at, for example, abutting termini of the tandem compounds:

an internally-situated non-complementary portion, non-nucleoside polyfunctional linkage units may be employed which have a backbone portion that forms a bridge of a desired steric length within the cleavage compound. The length of this bridging portion should be chosen to retain the overall complementarity of the cleavage compound with the target subregions of the target nucleic acid sequence so as to achieve stable hybridization. The bridging portion is generally flanked by two coupling groups for binding to the adjacent nucleosides in the cleavage compound sequence. Alternatively, the non-complementary portion may be positioned at a terminus of the cleavage compound using similar or analogous chemical techniques. Thus, non-complementary-non-nucleoside bridging or terminal groups may be used having structures such as:

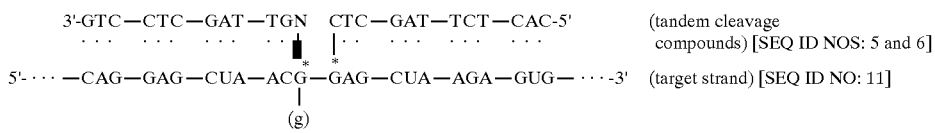

(tandem cleavage compounds) [SEQ ID NOS: 5 and 6]

(target strand) [SEQ ID NO: 11]

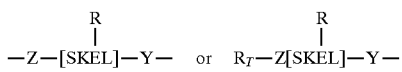

wherein SKEL comprises a non-nucleotide skeleton of from 1 to about 20 carbon atoms; Y is —CH$_2$—, —O—, —S—, —NH— or a bond; Z is —O—, —S— or —NH—; R is a group that is non-complementary to a purine or a pyrimidine base; and R$_T$ is hydrogen or a blocking group. Either or both of Y and Z may be coupled to the rest of the oligonucleoside backbone by a structure such as a phosphodiester group, a modified phosphorus-containing group, or other coupling group such as described in WO 92/02532 or in the "Definitions" section above. Preferred bridging and terminal groups include those of the following structures:

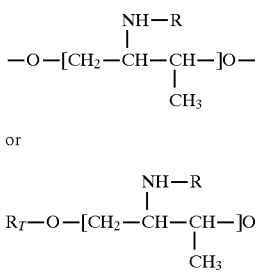

If utilized, an intercalating agent or other steric group may be bound to the backbone of the cleavage compound by way of any suitable bond, as for example an amide grouping formed with an amine linker arm attached to the cleavage compound. Here again, methods are known in the art to perform such conjugation reactions. See, e.g., PCT Publication No. WO92/02532.

It will be understood that cleavage may be accomplished according to the present invention using cleavage compounds that do not incorporate a specific non-complementary portion, particularly where a cleavage moiety having sufficient intrinsic cleavage activity is used. We discuss next in more detail the cleavage moiety aspect of the invention.

C. Preferred Cleavage Moiety Portions

The present cleavage compounds include compounds that incorporate a non-nucleoside or modified nucleoside cleavage moiety at a position which, when the cleavage compound is hybridized to the target sequence, is sufficiently proximate to a targeted internucleotidyl phosphodiester bond as to promote its cleavage. The cleavage moiety may be incorporated into the cleavage compound using a linker group which attaches the cleavage moiety to the remainder of the cleavage compound. Thus, the cleavage moiety may be appended via a nucleoside base linker group (e.g., a modified cytidine or guanosine base), or via a non-base linker group (e.g., an intercalator or linker-arm, for example amide or ester-based hydrocarbon chain linker arms) at a position in the cleavage compound that is positionally complementary to the particular phosphodiester bond targeted for cleavage. Alternatively, the cleavage moiety may be appended at a position in the cleavage compound that is separated by one or more nucleosidyl units from the phosphodiester bond that is to be cleaved, in which case the appendage point of the cleavage moiety will not be positionally complementary to the targeted phosphodiester bond. In either case, the linker group connecting the cleavage moiety to the remainder of the cleavage compound will have a size and conformation that allows the cleavage moiety to assume a position that is proximate to the phosphodiester bond (or bonds) targeted for cleavage when the cleavage compound is hybridized to the target nucleic acid sequence.

Chemical synthesis methods and linker groups for conjugating the cleavage moiety to the cleavage compound are available in the art. In general, the techniques for linking cleavage moieties may be similar to known techniques for linking labels or other groups to functional groups on proteins. See, e.g., G. M. Means and R. E. Feeney, *Chemical Modificaitons of Proteins* (Holden-Day Inc., 1971); R. E. Feeney, *Int. J. Peptide Protein Res.* 1987; 29:145–161. Preferably, the methods of commonly-assigned, copending U.S. patent application Ser. No. 08/068,140 (filed May 26, 1993) and Publication No. WO92/02532 may be employed. One preferred technique is described in Examples 4 and 5, in which the "C2" non-nucleoside bridging group described in WO92/02532 is used to link a cleavage compound with a variety of cleavage moieties. Example 7 describes one technique for linking a cleavage moiety to a modified nucleoside base in the cleavage compound. Linker arms having a suitable length (e.g., hydrocarbon chain linker arms) may usefully be employed. Attachment of the cleavage moiety may be achieved using coupling reactions known in the art, as for example by reacting an amine (e.g., alkylamine) group with a reactive ester, imine, aldehyde, acid halide, aryl halide, epoxide, aziridine, (iso)thiocyanate or sulfonyl moiety; or reacting a thiol group with a reactive haloacetyl, haloacetamide, disulfide, maleimide, arylmercury or sulfonyl moiety; or reacting a hydroxyl group with a reactive acid halide, ester, epoxide, aziridine or sulfonyl moiety. Attachment may be made to a methylene group in the cleavage portion, as for example to a methylene carbon of a polyfunctional macrocyclic metal complexing (e.g. chelating) agent. Suitable protecting groups will generally be employed to protect the other cleavage-enhancing groups on the cleavage moiety, or other reactive groups, during coupling (see, for example, E. Gross and J. Meienhofer (eds.), *The Peptides: Analysis and Synthesis, Biology*, Vol. 3 (Academic Press, 1971)). Other methods will be discernable given the teachings of the present disclosure.

As noted above, the cleavage moiety may be located internally within the overall oligonucleoside sequence of the cleavage compound, or it may be located at a terminal position. Furthermore, multiple cleavage moieties can be employed in a single cleavage compound, or in tandem cleavage compounds. A cleavage compound including a cleavage moiety may additionally incorporate a non-complementary portion, or it may be used in tandem with a second cleavage compound that incorporates a non-complementary portion.

In one embodiment, the presence of a cleavage moiety in the present compounds increases the cleavage of the target nucleic acid by functionally mimicking the active site of naturally-occurring RNases. The RNases have hydrolytic turn-over rates which approach $10^5$/minute. Even though the RNase cleaving mechanism is not completely understood, it is generally believed that two histidine (or other positively-charged amino acid) residues in the active site synchronously deprotonate the 2'-OH and protonate the 5'-oxygen of the phosphonate group, while both orienting the 2'-OH for attack on the phosphorus and stabilizing the cleavage intermediate by charge neutralization, proton exchange, and/or hydrogen bonding effects. The 2'-O group forms a cyclic phosphate upon elimination of the leaving 5'-OH portion, and this cyclic structure may thereafter be hydrolyzed to result in a 2'-hydroxy-3'-phosphate structure at the cleaved 3'-terminus.

While the non-complementary portion of the present compounds is chosen to orient the 2'-OH of the targeted internucleotide bond for nucleophilic attack, the cleavage moiety is chosen to act cooperatively to deprotonate the 2'-OH and protonate the leaving 5'-oxygen. Polyfunctional acid-base groups are particularly favored for the cleavage moiety. In addition, it is preferred that the cleavage moiety serve as a proton-donor, or electron-acceptor, with respect to at least one of the lone oxygen atoms of the phosphate target. The donation of a proton, as by a general base group on the cleavage moiety, is believed to facilitate cleavage by allowing formation of an intermediate protonated phosphate diester. These functions may be achieved by one or more groups that also afford charge neutralization or hydrogen bonding (as for example in the case of a polyamino cleavage moiety, as discussed below). Alternatively or additionally, the action of the cleavage moiety in the manner of an electrophile or Lewis acid group may serve to activate the phosphate center for nucleophilic attack by, for example, the deprotonated 2'-OH of the adjacent sugar group. This may be achieved by a highly active cleavage moiety such as a complexed (e.g. chelated) metal ion which acts as a Lewis acid/electrophile, and which enhances hydrolytic attack by in situ water or hydroxide ion.

One suitable class of cleavage moieties are amine-containing moieties, such as polyamino groups. As is described in detail in Example 1 below, compounds containing diamine moieties separated by two carbons are capable of catalytically hydrolyzing RNA, whereas compounds containing either a single amino group or two amino groups separated by more than two carbons are evidently not catalytic. These data support the conclusion that the cleavage moiety should, in one embodiment, be designed to possess a proton-donor group and proton-acceptor group on the same molecule. Furthermore, the spatial relationship of these proton-donor and acceptor groups should be selected so as to provide a structure which stabilizes the transition state intermediate of the hydrolysis or transesterification reaction, as described in more detail below.

A proton-acceptor group, if present in the cleavage moiety, will serve in a base-catalysis fashion to increase local pH around the target RNA strand and deprotonate the 2'-OH. The RNA backbone is cleaved by base hydrolysis as a result of this ionization and subsequent attack by the nucleophilic, deprotonated 2'-OH on the phosphodiester backbone. This pH effect is so pronounced that, at high pH, RNA is not stable for more than a few minutes. By placing cations close to the phosphodiester backbone, it is possible to increase the local pH and increase the rate of target RNA hydrolysis.

The cleavage moiety is also preferably capable of stabilizing the transition-state intermediate of the hydrolysis. This may be accomplished by a structure which affords hydrogen bonding and/or charge neutralization of the intermediate structure. See generally Jubian, et al., *J. Am. Chem. Soc.* 1992; 114:1120–1121, which is incorporated by reference, and which discusses aspects of stabilization of a trigonal-bipyramidal intermediate. Likewise, incorporation of a proton-donor group to protonate the 5'-oxygen serves to pull electron charge away from the phosphorus, increasing the rate of in-line displacement.

Particular polyfunctional cleavage moiety groups preferred for use in the present invention include polyamines such as the following:

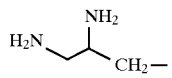

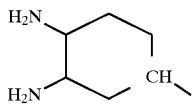
[Ethylenediamine]

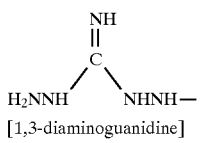
[1,2-diaminocyclohexane]

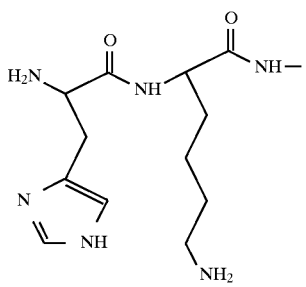
[1,3-diaminoguanidine]

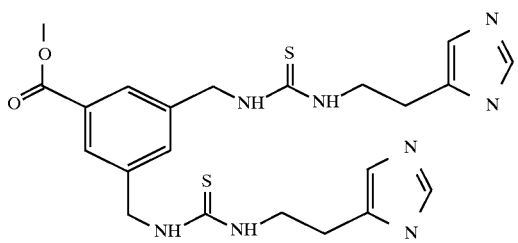
[His — Lys dipeptide]

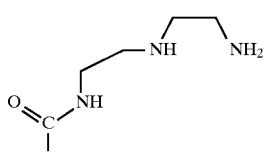
[Bis-(alkylthioureahistidine)-isophthalate]

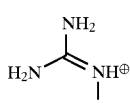
[1-oxo-2,5,8-triazaoctane]

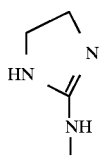
[guanidine]

[ethylene guanidine]

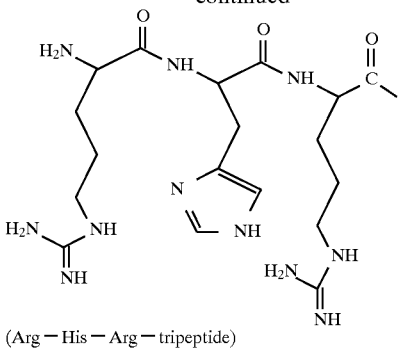

(Arg — His — Arg — tripeptide)

It will be understood that these cleavage moieties may be attached to the remainder of the cleavage compound using attachment points other than those illustrated above.

In an alternative embodiment of the present invention, the cleavage moiety may comprise a nucleophilic group which itself is capable of attacking the phosphorus atom of the target internucleotide bond. In this case, the 2'-OH of the neighboring sugar group is not the attacking nucleophile. Hence, the result of this cleavage reaction is transesterification (rather than hydrolysis), wherein the cleavage moiety becomes esterified to the 3'-phosphate group of the cleaved strand. (In contrast, in the case of intramolecular nucleophilic attack by the depronated 2'-OH group, an intermediate cyclic phosphate ester is formed following cleavage of the leaving 5'-OH group; this cyclic phosphate may thereafter be cleaved by hydrolysis to yield the final 2'-hydroxy-3'-phosphate hydrolysis cleavage product.) If the cleavage moiety is subsequently hydrolyzed from the cleaved target strand fragment, the result of this mechanism is the same as that obtained when the 2'-OH group is the attacking nucleophile.

When a single cleavage compound is to be used to accomplish the intended cleavage (i.e., when the compound is not being used in tandem with another cleavage compound), then the cleavage compound will preferably include a non-complementary portion in addition to its cleavage moiety portion, as part of a nucleoside sequence that is substantially complementary to the target nucleic acid sequence. In this case, the non-complementary portion and the cleavage moiety portion of the cleavage compound will be positioned proximately with respect to one another within the cleavage compound, such that the nucleotide on the target nucleic acid strand that loops or bulges out by operation of the non-complementary portion will be close enough to the cleavage moiety as to undergo the cleavage-enhancing effects of the cleavage moiety.

In practice, the cleavage moiety may be directly across from (i.e., positionally complementary to) the looped-out nucleotide of the target strand, as for example where the cleavage moiety is attached directly to an intercalating group or other non-complementary portion of the cleavage compound. See Example 5 below. In another example, a cleavage moiety may be attached to one (or both) of the two adjacent complementary nucleosides between which a complementary nucleoside has been omitted according to the "bulge-out" motif as described above. See Example 7 below. Alternatively, the cleavage moiety may be separated from the non-complementary bridging portion by one or more nucleoside units in the cleavage compound, or it may be situated on a separate tandem cleavage compound. In any case, the cleavage moiety will be linked to the cleavage compound via a linking group that is of sufficient size to allow the cleavage moiety to span across the inter-strand region, or between successive turns of the helical cleavage compound/target sequence duplex, thereby to effect cleavage of a phosphodiester bond associated with the looped-out or bulged-out nucleotide of the target sequence. The synthetic technology of PCT Publication No. WO 92/02532 may be employed to accomplish such structures.

It will be recognized that linking groups and/or steric groups (e.g., intercalating agents) of different sizes or structures may be employed, and that a variety of points of attachment for the cleavage moiety may be utilized. Those skilled in the art, given the present disclosure, will be able to identify suitable cleavage moiety attachment schemes which meet the requirements of the present invention.

In this regard, some of the preferred intercalator-cleavage moiety groups according to the invention include the following:

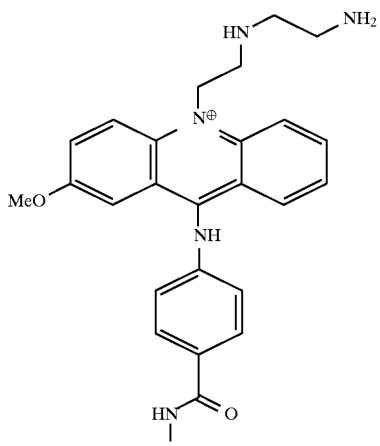

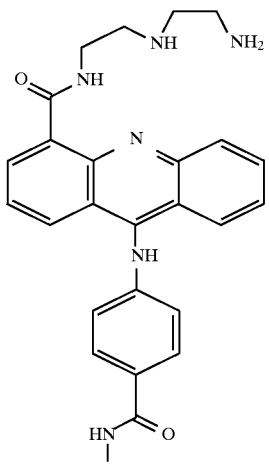

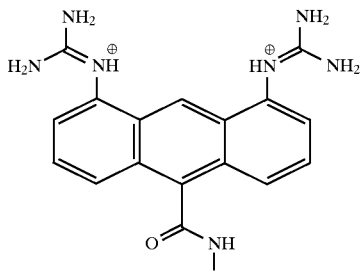

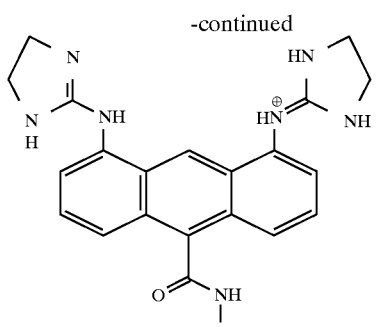

Groups such as the foregoing can be conjugated to the rest of the cleavage compound (particularly, the skeleton or backbone portion) via the amino radical shown above. Synthetic technology as described in, for example, PCT Publication No. WO92/02532 may be used to accomplish the desired structures. Other particularly preferred choices of cleavage moieties are described in detail herein, and may likewise be used in conjugation with intercalators or other steric groups.

As described above, the cleavage moiety may be conjugated as an adduct to a nucleoside-type base, e.g. a purine or pyrimidine base, or to an analog or modified form thereof, so as to form a modified nucleoside-type unit within the cleavage compound. Such a base adduct may, for example, take the form of a cytidine or guanosine adduct with a linear or branched polyamine. As above, it is preferred that the non-complementary portion (for example, an omitted complementary nucleoside or a mismatch bridging or terminal group) and the cleavage moiety portion be positioned within the cleavage compound in relatively close proximity to one another, particularly in neighboring or near-neighboring positions within the oligonucleoside sequence.

Where a single (i.e., non-tandem) cleavage compound is used having a cleavage moiety at an internal (i.e., non-terminal) position in the oligonucleoside sequence, the compound may effect cleavage in a catalytic fashion. After the compound has cleaved the target strand at the target site, the target strand portions may tend to dissociate from the hybridized duplex structure due to the instability introduced by the target bond. Because the cleavage compound remains structurally intact following hybrid dissociation, the compound can then act to cleave another target strand. This catalytic effect will not be as pronounced if the cleavage moiety is terminally-situated in the cleavage compound, because substantial complementarity will still exist, even after cleavage, between the target region of the severed strand and essentially the full length of the cleavage compound oligonucleoside sequence, and hybrid dissociation will be slower. However, while a catalytic mechanism may be useful in some instances, it is not considered to be necessary for many applications of the present invention.

Through the use of multiple cleavage moieties in a single cleavage compound or in tandem compounds, it is possible to enhance the cleavage activity of the oligonucleoside by incorporating multiple or multi-site nucleophilic or pH-increasing groups, transition-state stabilizing groups, charge neutralizing groups, etc. Furthermore, the respective multiple cleavage moieties can be chosen such that the first cleavage moiety provides some one or more of the desired activities (e.g., pH increase) while the second cleavage moiety provides other activities (e.g., transition state stabilization). If such cleavage moieties are in close proximity within the oligonucleoside, and particularly within proximity to the rotated-out nucleotide unit of the target strand, they may act to increase the cleavage effect at a particular site in the target RNA. Likewise, if multiple cleavage moieties are located at separated sites within the oligonucleoside they may act to cleave the target RNA at more than one site provided they can attain proximity to a phosphodiester bond on the target strand that is oriented for cleavage according to the present teachings, and thus increase the efficacy of the subject compounds.

Where multiple (i.e., tandem) cleavage compounds are used, or in some cases where the cleavage moiety has a high intrinsic cleavage capability (as discussed hereafter), cleavage compounds can be utilized which do not incorporate a non-complementary portion. Thus, as described above, the first cleavage compound of a tandem pair may include a cleavage moiety (but not a non-complementary portion) while the second tandem compound does have a non-complementary portion. The two (or more) tandem compounds are then used in combination to effect cleavage. Furthermore, single cleavage compounds that contain a non-complementary portion (but no cleavage moiety) may also be usefully employed to study the activity of non-oligonucleoside-bound cleavage moiety reagents or other active agents as demonstrated in Examples 3 and 9 below. Such studies are useful in identifying cleavage moieties for eventual incorporation into cleavage compounds of the invention, or for other study purposes (particularly in vitro).

In another preferred embodiment of the invention, the cleavage compound may include a strong Lewis acid or electrophilic cleavage moiety which serves to activate the phosphate center of the target internucleotide bond by electron-withdrawing effects. If the Lewis acid character of the cleavage moiety is substantial enough, cleavage may be achieved even if no non-complementary portion is utilized, and even in the absence of the other cleavage moiety functions described above. The mechanism of activity of this approach is believed to involve direct hydrolytic attack by in situ water or hydroxide ion on the activated phosphate center, rather than intramolecular attack by the 2'-OH group. It will be seen that this Lewis acid mechanism of activity does not require the trigonal-bipyramidal orientation associated with a "looped" or "bulged" out base as described above. Further, this mechanism may not require any or all of the separate cleavage moiety structures associated with 2'-OH deprotonation, acid-base or hydrogen bonding stabilization, or 5'-oxygen protonation as described above.

One especially preferred Lewis acid type cleavage moiety is a conjugated metal ion moiety, particularly a complexed (e.g. chelated) metal ion moiety. Preferred are chelated zinc moieties, particularly (1,5,9-triazododecane)$^{2+}$ chelated zinc. Studies (see Examples 8 and 9 below) have demonstrated that Zn[1,5,9-triazododecane]$^{2+}$ is useful in site-specifically cleaving a target RNA strand that is hybridized to a separate cleavage compound oligonucleoside containing an internally-situated non-complementary portion, and in cleaving a single-strand RNA target non-specifically in the absence of hybridization. Likewise, other metal ions, such as lanthanides, or bimetallic structures (see Steitz & Steitz,

*Proc. Natl. Acad. Sci. USA* 1993; 90:6498–6502), may be used. Of particular interest are macrocyclic chelated ions such as the europium (III) complex of 1,4,7,10-(2-hydroxyethyl)-1,4,7,10-tetraazacyclododecane (Eu[THED]), as described in Morrow and Chin, *Inorg. Chem.*, 1993; 32:3357–3361.

D. Tandem Cleavage Compounds

If two different cleavage compounds are to be used in tandem to accomplish the intended cleavage, then it is possible, for example, to incorporate the non-complementary portion in one of the two tandem cleavage compounds of the pair, and the cleavage moiety in the other tandem cleavage compound. At least one, and preferably both, of the tandem cleavage compounds will incorporate a nucleoside sequence that is substantially complementary to a target subregion of the target nucleic acid sequence. The respective complementary nucleoside sequences are preferably chosen such that both tandem cleavage compounds will hybridize simultaneously to subregions of the target nucleic acid sequence (or otherwise in proximity to the target internucleotidyl bond), and proximately to one another, whereby the non-complementary portion and the cleavage moiety portion of the tandem cleavage compounds, when so hybridized, are proximately positioned with respect to one another and also with respect to the target internucleotidyl bond. This proximate or adjacent positioning of the non-complementary and cleavage moiety portions of the tandem cleavage compounds allows the compounds to act in tandem to loop out a base on the target nucleic acid strand and, proximately thereto, to catalyze or promote cleavage of a phosphodiester bond of the target sequence.

The tandem cleavage compounds of the invention are preferably each individually complementary to neighboring target subregions of the target nucleic acid sequence. In this case, a non-complementary portion of a first tandem cleavage compound may be positioned at or near one terminus (e.g., the 3'-terminus) of the first tandem cleavage compound. A cleavage moiety portion of the second tandem cleavage compound may then be positioned at or near the 5'-terminus of the second tandem cleavage compound. When the two tandem cleavage compounds are hybridized to the neighboring complementary subregions of the target nucleic acid strand, the 3'-terminus of the first tandem compound will be in proximity to the 5'-terminus of the second tandem compound. Likewise, the non-complementary and cleavage moiety portions at the "abutting" termini of the respective tandem cleavage compounds will be adjacent or proximate to one another so as to effect cleavage of the target strand. Tandem cleavage compounds according to these and other approaches are depicted in the foregoing description.

Alternatively, each tandem cleavage compound may include a "mating" subportion which is complementary to a corresponding mating subportion of the other tandem cleavage compound, and one or both tandem cleavage compounds may further include a separate "targeting" subportion which is substantially complementary to a distinct target subregion of the target nucleic acid strand. Preferably, both tandem cleavage compounds will contain a targeting subportion, and the two corresponding complementary target subregions of the target strand will be neighboring or adjacent to one another within the overall targeted region of the target strand. In this manner, hybridization will occur between the respective mating subportions of the tandem cleavage compounds that are complementary to one another, and the remaining targeting subportions of the cleavage compounds will each further hybridize to the respective complementary target subregions of the target nucleic acid strand to form a non-complementary "three-way junction" structure with the target strand. Such a structure may be depicted schematically as follows:

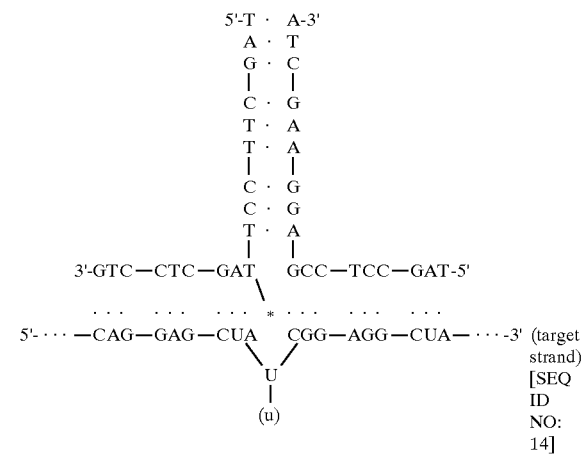

Both a cleavage moiety (*) and a non-complementary portion (formed by the omission of any base at the junction point of the tandem compounds that would be complementary to the thymine base on the target strand) are included in the mating tandem cleavage compounds depicted above [SEQ ID NOS:12 and 13]. As should be clear by now from the foregoing description of the invention, the non-complementary structure and the cleavage moiety portion of the mated tandem cleavage compounds are positioned such that they are proximate to one another, and to the target site on the target nucleic acid strand, when the final hybridized structure is formed. As above, an intercalator or other steric group may be used in conjunction with the non-complementary portion, and a cleavage moiety may be attached thereto. Multiple cleavage moieties may be employed.

This three-way junction configuration is believed to be particularly advantageous because the junction point of the final hybridized structure will strain the backbone of the target nucleic acid sequence and facilitate the rotation of a base at the target site by, for example, reducing inter-base stacking forces. In fact, it is believed that the target strand in the final three-way junction structure (prior to cleavage) will be "bent" at the junction point such that the three duplexed "arms" of the structure are angled roughly 120° from one another (rather than in right angles as in the above schematic depiction). Because of this strain effect, it may not be necessary to include any supplemental non-complementary steric group (e.g., intercalating group) in either of the two tandem cleavage compounds. Likewise, as shown above, a base-omission type non-complementary structure may be achieved at the junction point of the hybridized tandem compounds, resulting in a bulge-out effect at the target site.

Alternatively, as depicted below, only one of the two tandem cleavage compounds will contain a targeting subportion.

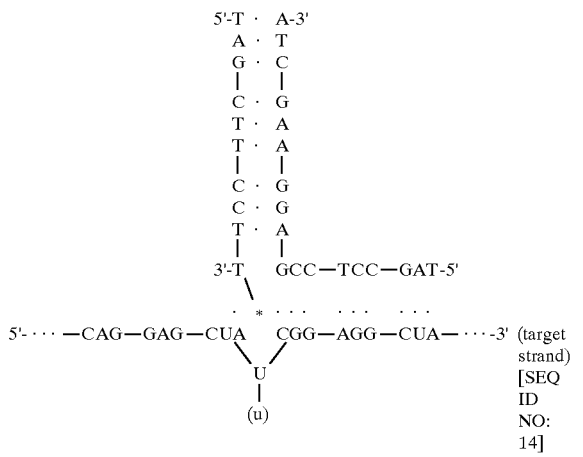

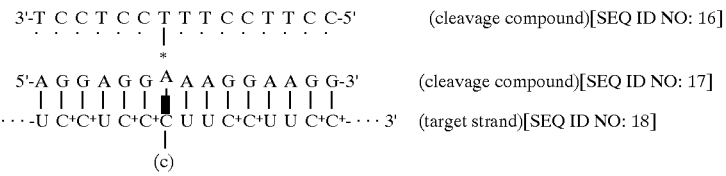

In this case, the left-most tandem cleavage compound that does not contain a targeting subportion [SEQ ID NO: 15] will be held in proximity to the target internucleotidyl bond by virtue of its being hybridized, via its mating portion, to the other cleavage compound [SEQ ID NO:13] of the tandem pair.

In a variation of the three-way junction tandem cleavage compound motifs just described, the two "tandem" compounds may be covalently linked to one another, as for example by a hairpin structure bridging the two mating subportions of the tandem pair. Thus, in the two depictions above, the 5'- and 3'- termini of the cleavage compounds at the top "arm" of the structure may be linked in a hairpin fashion via a sequence of additional nucleosides.

As described above, more than two tandem cleavage compounds may be used together. For example, a series of three tandem compounds may be used which are substantially complementary to three neighboring subregions of the target strand. In this case, the "middle" tandem compound may have two cleavage moieties, one situated at each of its termini, and the two "surrounding" or laterally-hybridized tandem compounds may each have a non-complementary portion situated at the respective terminus that abuts or mates with the middle tandem compound in the final hybridized structure. As above, the non-complementary portion(s) may be omitted and/or supplemented with an additional cleavage moiety. Further structural variations will also be recognized given the teachings of the present disclosure.

It will further be recognized that the chemical moieties, and the synthetic methods, referred to above will also be useful in designing and making tandem cleavage compounds.

E. Triple-Strand Structures

The cleavage compounds of the invention may also be designed to achieve triple-strand binding with a target nucleic acid single-strand. Thus, two tandem cleavage compounds are chosen each with a common nucleoside sequence, or each with a different nucleoside sequence, such that the tandem compounds have substantial triple-strand complementarity with a selected target region of the target nucleic acid single-strand. In this event, the non-complementary portion (if present) and the cleavage moiety portion may be included, respectively, on separate tandem cleavage compounds. An example of such structures may be depicted as follows:

A variation of the three-way junction-type tandem cleavage structures described above may also be achieved using triple-strand hybridization techniques. As depicted below, a cleavage moiety may be positioned at or near the terminus of a single-strand oligonucleoside "mating" sequence which is capable of triple-strand hybridization with one or both "mating" subportions of two additional tandem cleavage compounds. In this fashion, the cleavage moiety will be held in proximity to the target bond site of the target mRNA strand at the junction point of the resulting three-way junction structure.

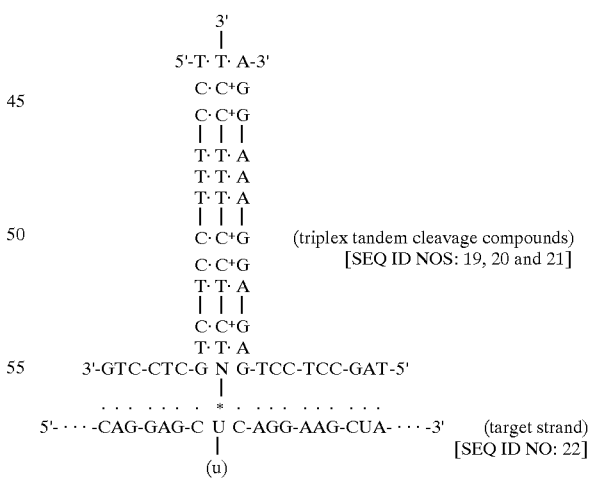

In the above schematic depiction, both a non-complementary portion (which may be, for example, an omitted complementary base or a steric group) and a cleavage moiety are present in the same "middle" strand of the triple-strand structure. As will be evident from the descriptions above, a non-complementary structure may otherwise be formed at the junction of the three triplex-forming cleavage compound strands, as for example where the guanosine nucleoside at the junction point of the right-most tandem compound is omitted and a base-modified adenosine nucleoside (linked with a cleavage moiety) is substituted for the non-complementary unit in the middle tandem compound. (In this case, the cytidine nucleotide that is on the 3'-side of the central uridine in the target strand will "bulge" out from the duplexed target strand backbone, and the central uracil base will no longer be rotated out.) Likewise, the cleavage moiety may be situated on a different cleavage compound, or multiple cleavage moieties may be employed. A hairpin-type structure may additionally be utilized, as described above in connection with the double-strand three-way junction tandem cleavage compounds.

As above, the sequences depicted in these schematic drawings are illustrative only. Examples of the selection and use of oligonucleoside sequences to achieve triple-strand hybridization are described in U.S. patent application Ser. Nos. 07/772,081 (filed Oct. 7, 1991) and 07/987,746 (filed December 8, 1992). These teachings may be usefully employed in the practice of the present invention given the present disclosure. It will also be recognized that the synthetic schemes and functional and structural considerations referred to above are also relevant to the design and use of triple-strand cleavage compounds.

F. Therapeutic Uses

Many diseases and other conditions in multicellular organisms, particularly mammals including humans, are characterized by the presence of undesired DNA or RNA, which may in certain instances be in single-stranded form and in other instances in double-stranded form. These diseases and conditions can be treated using the principles of anti-sense therapy as is generally understood in the art.

According to the methods of the present invention, a hybrid complex is formed having a sufficiently high degree of selectivity and affinity as to interact with the target strand of interest. The cleavage compounds may be used to detect or locate and then irreversibly modify the target site in the nucleic acid by cleaving the RNA. By careful selection of a target site for cleavage, the oligonucleotide strand may be used as a molecular scissors to specifically cleave a selected nucleic acid sequence.

These cleavage compounds may be used to inactivate, or to inhibit or alter, expression of a particular gene or target sequence in a living cell, thus allowing selective inactivation, inhibition or alteration of expression. The target sequence may be RNA, such as pre-mRNA, a mRNA or an RNA sequence such as an initiator codon, a polyadenylation region, an mRNA cap site or a splice junction.

The cleavage compounds for use in the instant invention may be administered singly, or tandem or separate combinations of the compounds may be administered for adjacent or non-neighboring targets or for combined effects of anti-sense mechanisms in accordance with the foregoing general mechanisms. The oligonucleotide compounds may be administered in any convenient vehicle that is physiologically acceptable. In therapeutic applications, the cleavage compounds can be formulated for a variety of modes of administration, including systemic, topical or localized administration. Techniques and formulations generally may be found in *Remington's Pharmaceutical Sciences*, Mack Publishing Co., Easton, Pa., latest edition. In each case, a therapeutic amount of the cleavage compound is administered when the normal translation of the target nucleic acid is to be prevented. The cleavage compound is generally combined with a carrier such as a diluent or excipient which may include fillers, extenders, binding, wetting agents, disintegrants, surface-active agents, or lubricants, depending on the nature of the mode of administration and dosage forms. Typical dosage forms include tablets, powders, liquid preparations including suspensions, emulsions and solutions, granules, capsules and suppositories, as well as liquid preparations for injections, including liposome preparations.

For systemic administration, injection may be preferred, including intramuscular, intravenous, intraperitoneal, and subcutaneous. For injection, the cleavage compounds of the invention are formulated in liquid solutions, preferably in physiologically compatible buffers such as Hank's solution or Ringer's solution. In addition, the compounds may be formulated in solid form and redissolved or suspended immediately prior to use. Lyophilized forms are also included. In some instances, the compositions may be infused upstream from the site of the cells whose activity is to be modulated. The localized concentration or amount administered may be determined empirically and will depend upon the purpose of the administration, the area to be treated, the effectiveness of the composition, and the manner of administration. The localized concentration will desirably be in the range of about 1 to 50 μM, or lower if appropriate. Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents may be used to facilitate permeation. Transmucosal administration may be through use of nasal sprays, for example, as well as formulations suitable for administration by inhalation, or suppositories. For oral administration, the oligonucleosides are formulated into conventional as well as delayed release oral administration forms such as capsules, tablets, and tonics.

For topical administration, the oligonucleosides for use in the invention are formulated into ointments, salves, eye drops, gels, or creams, as is generally known in the art.

The following examples are included by way of illustration and are not intended to limit the scope of the invention.

EXAMPLE 1

Method for Screening Compounds which Catalyze the Hydrolysis of RNA at Physiological pH The RNA target oligonucleotide used in these studies was an 18-base alternating co-polymer of cytidine and uridine having a single purine base at the 3'- and 5'-ends:

R183=5'-rACUCUCUCUCUCUCUCUG-3'

This oligonucleotide [SEQ ID NO:23] was labelled with $^{32}$p according to the following protocol. A 1 μM solution was prepared in 10 mM Tris-HCl, 1 mM EDTA (pH 7). To 2 μL of this solution (20 pmoles) was added 2 μL of 10× kinase buffer (US Biochemicals, Inc.), 5 μL of [γ-$^{32}$p] ATP (50 μCi, 3000 Ci/mmol), 10.5 μL of sterile deionized water, and 0.5 μL of T4-polynucleotide kinase (15 units, Boehringer-Mannheim, Inc.). The reaction mixture was incubated at 37° C. for 30 minutes. The resulting $^{32}$P-labelled RNA oligonucleotide was purified by chromatography on a Nensorb™-20 cartridge (NEN/DuPont) according to the manufacturer's instructions.

The general method for screening compounds for potential cleavage activity was as follows. Aliquots of $^{32}$P-labelled RNA corresponding to about 200,000 cpm (Cerenkov radiation) were pipetted into sterile polypropylene microfuge tubes (PCR type) and dried in a Speed-Vac™ evaporator (Savant, Inc.). The dried samples of $^{32}$P-labelled RNA were then resuspended in 10 μL of an aqueous solution of the test compound (1M, pH 7 as the HCl salt) and incubated at 50° C. for 16–24 hours. Next, 2 μL aliquots were removed and diluted with 10 μL of 90% formamide in 1× TBE buffer (89 mM Tris-borate, 25 mM EDTA, pH 8.2) containing 0.1% bromphenol blue dye. The resulting samples were applied to a 20% polyacrylamide (19.1 acrylamide/bisacrylamide)/7M urea gel (0.5 mm thick×20 cm wide×30 cm long) containing 1× TBE buffer. This gel was electrophoresed at 100–1200 volts until the bromphenol blue dye had progressed about two-thirds of the distance down the gel (about 2-½ hours). Next, the wet gel was covered with plastic wrap and exposed to XAR-5 film (Eastman-Kodak) for 15–30 minutes. The autoradiographs contained either a single band corresponding to the full-length RNA oligomer (no hydrolysis) or a ladder of bands corresponding to shorter oligomers having cleavages at various locations in the sequence. The relative intensities of the bands corresponding to hydrolyzed portions were compared to those of the full-length (unhydrolyzed) strands to estimate the relative catalytic potential of each test compound.

A large number of different compounds were screened for catalytic activity with synthetic RNA according to this example. Peptides and amino acids were obtained from Sigma Chemical Co. and used without purification. All other compounds were purchased from Aldrich Chemical Co. All solutions were adjusted to pH 7 with hydrochloric acid except for ammonium acetate, which was prepared from the HPLC grade salt. All solutions were sterilized by autoclaving prior to analysis. Water used to prepare these solutions was treated with diethylpyrocarbonate to remove ribonuclease contamination according to the procedures given in S. L. Berger and A. R. Kimmel, Methods in Enzymology, Volume 152, "Guide to Molecular Cloning Techniques", Academic Press, Inc., 1987. Representative results are summarized in Table 1.

TABLE 1

Relative rates of RNA hydrolysis catalyzed by various compounds according to the procedure given in Example 1.

| Compound | Relative Hydrolysis Rate |
|---|---|
| Ethylenediamine | +++++ |
| 1,2-diaminocyclohexane | +++++ |
| 1,3-diaminoguanidine | ++++ |
| 1,2-diamino-2-methylpropane | +++ |
| 1,3-diamino-2-hydroxypropane | (none) |
| Tris-(2-aminoethyl)-amine | (none) |
| Propylamine | (none) |
| Ammonium acetate | (none) |
| Histidine-lysine dipeptide | ++++ |
| Lysine-arginine dipeptide | (none) |
| Arginine-lysine dipeptide | (none) |
| Lysine-tryptophane-lysine tripeptide | (none) |
| L-arginine | (none) |
| L-histidine | (none) |

Compounds containing diamino moieties separated by two carbons were catalytic according to this example. Compounds containing either a single amino group or two amino groups separated by more than two carbons were not catalytic. In addition, the histidine-lysine dipeptide was catalytic. This data supports the general conclusion that possession of a proton-donor and a proton-acceptor in the same molecule will support catalytic activity. For example, compounds containing two amino groups separated by more than two carbons are bis-protonated at physiological pH, whereas those having two amino groups separated by two carbons or less tend to be monoprotonated (due to charge-charge repulsion). Furthermore, the side chains of lysine and arginine tend to be protonated at physiological pH, whereas the histidine sidechain is near its pKa at this pH. Thus, only the histidine-lysine dipeptide of this example would be expected to contain both a proton-donor and a proton-acceptor at pH 7, whereas the other di- and tri- peptides would only be expected to contain proton acceptors.

In addition, a panel of tripeptides consisting of histidine (His), lysine (Lys) and arginine (Arg) subunits were screened for their ability to catalyze the hydrolytic cleavage of the $^{32}$P-labelled synthetic oligoribonucleotide R183. Reagents and experimental conditions were as described above except for the following modifications. Each tripeptide was provided as a 50 mM solution in 100 mM Tris-Acetate (pH 7). Solutions of tripeptide were incubated with $^{32}$P-labelled oligoribonucleotide R183 at 50° C. for 20 hours. Cleavage fragments were detected by polyacrylamide gel electrophoresis as described above. The following table summarizes the results.

TABLE 2

Relative rates of RNA hydrolysis catalyzed by various tripeptides

| Compound | Relative Hydrolysis Rate |
|---|---|
| Ethylenediamine.HCl (1M, pH 8) | ++++ |
| His—His—His (50 mM, pH 7) | (none) |
| His—His—Arg (50 mM, pH 7) | (none) |
| His—Arg—Arg (50 mM, pH 7) | (none) |
| His—His—Lys (50 mM, pH 7) | (none) |
| Lys—His—His (50 mM, pH 7) | (none) |
| Lys—His—Arg (50 mM, pH 7) | (none) |
| Lys—Lys—Arg (50 mM, pH 7) | (none) |
| Arg—His—Arg (50 mM, pH 7) | +++++ |
| His—Lys—His (50 mM, pH 7) | (none) |
| Lys—Arg—Arg (50 mM, pH 7) | (none) |

It was noted that only the Arg-His-Arg tripeptide appeared to catalyze hydrolytic cleavage of the RNA oligomer, and that it did so with good activity compared to EDA.

EXAMPLE 2

Decrease in the Rate of Hydrolysis of an RNA Oligonucleotide in the Presence of a Complementary Methylphosphonate Oligonucleoside The hydrolysis rates catalyzed by ethylenediamine were measured with the following RNA target oligonucleotide in the presence and absence of its complementary methylphosphonate oligonucleoside (MP-oligonucleoside).

RNA oligonucleotide=5'-CAG-GAG-CUA-AGG-AAG-CUA-3' (R197-1) [SEQ ID NO:2]

MP-oligonucleoside=3'-GTC-CTC-GAT-TCC-TTC-GAT-5' (1634-1) [SEQ ID NO:24]

The RNA oligonucleotide R197-1 was labelled with $^{32}$p according to Example 1. Aliquots containing about 200,000 cpm (Cerenkov radiation) were pipetted into sterile polypropylene microcentrifuge tubes (PCR type) and dried in a Speed-Vac™ evaporator. These samples were then resuspended in 10 μL of an aqueous solution of 1M ethylenediamine-HCl, pH 7, prepared according to Example 1. Two of the tubes also contained 50 μM of complementary MP-oligonucleoside 1634-1. Two of the tubes without MP-oligonucleoside were immediately frozen in dry ice and stored at 20° C. for use as time=0 controls. The remaining tubes were incubated at 25° C. for 46 hours. Next, the t=0 controls were thawed and 2 μL aliquots from each tube were diluted with 8 μL of 90% formamide in 1× TBE buffer (89 mM Tris-borate, 25 mM EDTA, pH 8.2) containing 0.1% bromphenol blue dye. The resulting samples were analyzed by polyacrylamide gel electrophoresis according to Example 1. The reaction mixtures containing MP-oligonucleoside had negligible hydrolysis compared to the t=0 controls, whereas those not containing MP-oligonucleoside were about 25% hydrolyzed.

EXAMPLE 3

Ethylenediamine-Catalyzed Hydrolysis of an RNA Target Strand in the Presence and Absence of a Complementary Methylphosphonate Oligonucleoside Containing a Non-Nucleotide, Non-Complementary Bridging Portion in Place of one of the Bases A methylphosphonate oligonucleoside (1719-1) was prepared with a non-nucleotide based non-complementary bridging portion replacing one of the nucleoside units in the methylphosphonate sequence presented in Example 2. This bridging moiety is designated C2, and has the following structure:

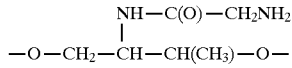

The preparation and incorporation of such non-nucleotide based bridging moieties is described in Reynolds et al., PCT Patent Publication No. WO92/02532 (published Feb. 20, 1992) and copending U.S. patent application Ser. No. 08/068,140, and is briefly set forth below:

(I) Reduction of L-Threonine Methyl Ester

L-Threonine methyl ester purchased from Sigma) was reduced according to the procedure of Stanfield et al., J. Org. Chem. 46:4799 (1981): in a 500 ml three-necked flask, 5 g of L-threonine methyl ester and 200 ml dry THF were mixed and 150 ml of 1M solution of $LiAlH_4$ was added dropwise with stirring while under argon. The reaction mixture was then warmed up to the boiling temperature of THF and refluxed under argon overnight. The completion of the reaction was monitored by thin layer chromatography (TLC) on silica gel which was visualized with ninhydrin. The reaction mixture was cooled to 5°–10° C. and quenched with dropwise addition of 0.25M NaOH (100 ml). The mixture was evaporated to remove over 90% of THF and the residue was diluted with 100 ml of dimethylformamide which facilitates the filtration. The mixture was then filtered through a Whatman #1 paper using aspirator vacuum. The filtrate was evaporated to dryness and the residue was purified on a flash silica gel column. The column was packed with dichloromethane and the product was eluted with 50% methanol in dichloromethane.

(II) Synthesis of 4-n-(9-Fluorenylmethoxycarbonyl)-4-Amino-n-Butyric Acid

Fmoc-aminobutyric acid (for C4 bridging moiety) was prepared according to the following procedure. Note: other Fmoc-aminocarboxylic acids are commercially available; for example, Fmoc-aminocaproic (for C6 bridging moiety) and Fmoc-glycine (for C2 bridging moiety) are commercially available from Bachem, Inc., Torrance, Calif.

A mixture of 1.8 g 4-aminobutyric acid and 1.24 g sodium hydrogen carbonate in 35 ml water/acetone (50:50) was prepared and 5 g Fmoc-succinimidyl carbonate (N-Fluorenylmethyl-succinimidylcarbonate) (Bachem) was added. The reaction mixture was stirred overnight at room temperature. The pH of the reaction mixture was adjusted to 2 by addition of 1N HCl and the solvent was removed under reduced pressure and the residue was dissolved in 20 ml ethanol and filtered. The filtrate was evaporated to dryness and the residue was taken up in dichloromethane and filtered to give 4.8 g of pure product.

$^1$H NMR in DMSO-d6, 1.61 ($CH_2$), 2.22 ($CH_2$), 3.01 ($CH_2$—N), 4.32 ($CH_2$—C=O), 4.22 (NH), 7.25–7.95 (8 aromatic protons).

(III) Blocking of the Amine Moiety of Reduced L-Threonine

The amine moiety of the reduced L-threonine was coupled with a 9-fluorenylmethoxycarbonyl ("Fmoc") group using a procedure similar to the Fmoc-aminobutyric acid preparation described above. After the overnight reaction, adjustment of the pH was not necessary. The solvent was removed and the residue was dissolved in 40 ml dichloromethane and extracted with water (2×50 ml). The organic phase was then dried and purified on a flash silica gel column. The product was eluted with 2% methanol in dichloromethane to give 3.85 g of the product.

$^1$H NMR 1.20 ($CH_3$), 2.85 (NH), 3.26 (CH), 3.48 (CH), 3.72 (OH), 7.3–7.9 (8 aromatic protons).

(IV) Preparation of Fmoc-Blocked Bridging Moieties: Fmoc-Glycylamido-Caproic Acid (C8), Fmoc-4-Aminobutrylamido-Caproic Acid (C10) and Fmoc-Caproylamido-Caproic Acid (C12)

Fmoc-glycine, Fmoc-aminobutyric acid and Fmoc-aminocaproic acid were coupled to the aminocaproic acid in order to synthesize the above-identified C8, C10 and C12 bridging moieties. The desired Fmoc-amino acid (17 mmol) was dried with co-evaporation with dry pyridine (3×30 ml). The dried material was then dissolved in 30 ml of dry dimethylformamide and 30 ml dry tetrahydrofuran was added. The solution was cooled to 0° C. and 1 equivalent (17 mmol) of N,N-diisopropylethylamine was added. While stirring, 1 equivalent of trimethylacetyl chloride was added dropwise at 0° C. and stirred for 45 min. 1.2 equivalents of dry aminocaproic acid was then added and the reaction mixture was warmed up to room temperature and stirred overnight. The progress of the reaction was monitored by TLC. After completion, the solvents were evaporated under reduced pressure. The residue was reconstituted with 50 ml water and the pH was adjusted to 2 by 1N HCl. The mixture was extracted with 100 ml of ethyl acetate and the organic phase was washed with 20 ml of water and dried ($MgSO_4$). The mixture was then filtered and the solvent was evaporated under reduced pressure to a volume of about 40 ml. Hexane was added dropwise to this solution until cloudiness and cleared by heating. The product was then crystallized overnight.

C8 $^1$H NMR in DMSO-d6, 1.30 ($CH_2$), 1.39 ($CH_2$), 1.48 ($CH_2$), 2.20 ($CH_2$—N), 3.06 ($CH_2$ of Fmoc), 3.58 ($CH_2$—COOH), 4.24 (2NH), 4.34 (CH of Fmoc and $CH_2$ of Glycine), 7.3-7.9 (8-Aromatic protons).

C10 $^1$H NMR in DMSO-d6, 1.30–1.70 (5$CH_2$'s), 2.07 ($CH_2$), 2.20 (CH—N), 3.0–3.1 ($CH_2$—COOH and $CH_2$ of Fmoc), 4.26 (2NH), 4.31 (CH of Fmoc), 7.3–7.9 (8-Aromatic protons).

C12 $^1$H NMR in DMSO-d6, 1.2–1.5 (6$CH_2$'s), 2.00 ($CH_2$—N), 2.18 ($CH_2$—N), 2.9–3.0 (2$CH_2$—C=O), 4.23 (2NH), 4.31 ($CH_2$ of Fmoc), 7.3–7.9 (8-Aromatic protons).

(V) Coupling of Reduced L-Threonine to Bridging Moieties

The desired bridging moiety (11 mmol), prepared as described above [Fmoc-glycine (C2), Fmoc-4-aminobutyric acid (C4), Fmoc-caproic acid (C6), Fmoc-glyclamidocaproic acid (C8), Fmoc-4-aminobutyrylamido-caproic acid (C10), and Fmoc-aminocaproylamidocaproic acid (C12)], was dried with co-evaporation with pyridine (3×20 ml). The dry residue was dissolved in 40 ml of a mixture of anhydrous dimethylformamide and anhydrous tetrahydrofuran (1:1). The solution was cooled in an ice bath and 1 equivalent of diisopropylethylamine was added. While stirring, 1.1 equivalents of trimethylacetyl chloride was added dropwise and stirred for 45 min at 0° C. A solution of 1.5 equivalents of reduced L-threonine (prepared as described above) was added and the reaction mixture was allowed to warm to room temperature and stirred for one hour. The progress of the reaction was monitored by TLC on silica gel which was developed by $CH_2Cl_2/CH_3OH/CH_3COOH$ (10:1:0.1) solvent system. After the completion of the reaction, the solvent was removed under reduced pressure and the residue was mixed with 50 ml ethyl acetate. The water soluble materials were removed by extraction with 40 ml saturated sodium bicarbonate. The organic phase was washed with 20 ml of water and dried with $MgSO_4$. The product was crystallized from ethyl acetate.

C2 Bridging Moiety $^1$H NMR in DMSO-d6, 1.03 ($CH_3$ of reduced L-threonine), 3.35 (OH), 3.3–3.45 (2CH), 3.91 (NH), 4.27 (other NH), 4.31 (OH), 4.34 ($CH_2$), 4.63 ($CH_2$ and CH of Fmoc), 7.3–7.9 (8-Aromatic protons).

C4 Bridging Moiety $^1$H NMR in DMSO-d6, 1.03 ($CH_3$ of reduced L-threonine), 1.62 ($CH_2$), 2.14 ($CH_2$), 2.91 (CH), 2.97 (CH2), 3.3–3.5 (2CH), 3.63 (OH), 3.84 (OH), 4.23 (CH), 4.33 (CH and $CH_2$ of Fmoc), 4.60 (NH), 6.32 (NH), 7.3–7.9 (8-Aromatic protons).

C6 Bridging Moiety $^1$H NMR in DMSO-d6, 1.03 ($CH_3$ of reduced L-threonine, 1.3–1.7 (3 $CH_2$'s), 2.52 ($CH_2$—N), 3.12 (CH—C=O), 3.8–3.9 (2 OH), 4.1–4.2 (2CH), 4.41 ($CH_2$ of Fmoc), 5.22 (NH), 6.48 (NH), 7.3–7.9 (8-Aromatic protons).

C8 Bridging Moiety $^1$H NMR in DMSO-d6 major proton signals are as follows: 1.01 ($CH_3$ of reduced L-threonine), 1.22–1.52 (3 $CH_2$ of caproate), 3.62 and 3.84 (2 OH), 5.35 (NH), 6.18 (NH), 7.3–7.9 (8-Aromatic protons).

C10 Bridging Moiety $^1$H NMR in DMSO-d6, 1.02 ($CH_3$ of reduced L-threonine, 1.3–1.50 (4 $CH_2$'s), 3.64 (OH), 3.82 (OH), 4.64 (NH), 6.33 (NH), 6.62 (NH), 7.3–7.9 (8-Aromatic protons).

C12 Bridging Moiety $^1$H NMR in DMSO-d6 major proton signals for identification 1.01 ($CH_3$ of reduced L-threonine), 1.30–1.50 (6$CH_2$'s), 3.63 (OH), 3.82 (OH), 4.62 (NH), 6.31 (NH), 6.63 (NH), 7.3–7.9 (8-Aromatic protons).

(VI) Dimethoxy Tritylation of the Primary Hydroxyl Moiety of the Non-Nucleotide Reagent The desired non-nucleotide reagent (6 mmol), which was prepared as described above, was dried by co-evaporation with dry pyridine and dissolved in 15 ml of dry pyridine. A solution of 2.2 g of dimethoxytrityl chloride in 20 ml of $CH_2Cl_2$/pyridine (1:1) was added dropwise with stirring. The reaction continued at room temperature for 45 min. The progress of the reaction was monitored by TLC. After the completion of the reaction, it was quenched by the addition of 2 ml methanol which was stirred for 10 min. The solvents were removed under reduced pressure and the residue was dissolved in 50 ml of dichloromethane and extracted with saturated sodium hydrogen carbonate (2×50 ml) followed by water (30 ml). The organic phase was dried with $MgSO_4$ and filtered. After the evaporation of the solvent, the residue was purified with flash column chromatography. The product was eluted with 2% methanol in dichloromethane containing 0.5% triethylamine.

C0 Bridging Moiety $^1$H NMR, $CDCl_3$, 1.18 ($CH_3$ of reduced L-threonine), 1.63 (CH), 2.83 (NH), 3.77 (2 $CH_3$ of DMT, 3.82 ($CH_2$ of Fmoc), 5.48 ($CH_2$—O-DMT), 6.82–7.90 (21 aromatic protons).

C2 Bridging Moiety $^1$H NMR, $CDCl_3$, 1.18 ($CH_3$ of reduced L-threonine), 3.78 (2 $CH_3$'s of DMT), 4.35 ($CH_2$—O-DMT), 5.98 (NH) 6.80–7.78 (21 (aromatic protons).

C4 Bridging Moiety $^1$H NMR, $CDCl_3$, major signals 1.18 ($CH_3$ of reduced L.-threonine), 1.83 ($CH_2$), 2.28 ($CH_2$), 3.74 (2 $CH_3$ of DMT), 4.21 (OH), 4.38 ($CH_2$ of Fmoc), 5.22 and 6.42 (2 NH), 6.80–7.65 (21 aromatic protons).

C6 Bridging Moiety $^1$H NMR, $CDCl_3$ major peaks 1.12 ($CH_3$ of reduced L-threonine), 1.3–1.6 (3 $CH_2$'s), 3.75 (2 $CH_3$ of DMT), 4.38 ($CH_2$ of Fmoc), 6.80–7.90 (21 aromatic protons).

C8 Bridging Moiety $^1$H NMR, $CDCl_3$ Major identifying signals were 1.12 ($CH_3$ of reduced L-threonine), 3.80 (2 $CH_3$ of DMT), 5.42 ($CH_2$ of FMOC), 6.18 and 6.321 (2 NH), 6.82–7.80 (21 aromatic protons).

C12 Bridging Moiety $^1$H NMR, $CDCl_3$ major identifying signals were 1.12 ($CH_3$ of reduced L-threonine), 3.78 (2 $CH_3$ of DMT), 4.59 ($CH_2$ of Fmoc), 6.80–7.8 (21 aromatic protons).

C10 Bridging Moiety $^1$H NMR, $CDCl_3$, 1.18 ($CH_3$ of reduced L-threonine), 3.78 (2 $CH_3$ of DMT), 4.40 ($CH_2$ of Fmoc), 6.8–7.8 (21 aromatic protons) all the $CH_2$ and CH (non-aromatics were also accounted for but not assigned).

(VII) Methylphosphinylation of the Secondary Hydroxyl Moiety of the Non-Nucleotide Reagents A DMT-blocked bridging moiety made according to the procedure described above (4 mmol) was dried by co-evaporation with dry pyridine and the residue was dissolved in 20 ml of anhydrous dichloromethane. Under closed argon atmosphere, 1.5 equivalents of diisopropylethylamine was added and 1.2 equivalents of N,N-diisopropylmethyphosphinamidic chloride [$(CH_3)_2CH]_2NP(CH_3)Cl$ was added dropwise. The reaction was completed in 45 min. The solvent was removed under reduced pressure and the residue was purified on a flash silica gel column. The column was packed with ethyl acetate/hexane (1:1) containing 5% triethylamine and washed with the ethyl acetate/hexane containing 1% triethylamine. The reaction mixture was then loaded on the column and the product was eluted with ethyl acetate/hexane (1:1) containing a 1% triethylamine.

Other non-nucleotide reagents are prepared by coupling of the bridging moiety-modified reagents made according to the methods described above with other phosphorylating agents such as N,N-diisopropylmethyl phosphonamidic chloride, $[(CH_3)_2CH]_2NP(OCH_3)Cl$, and 2-cyano-ethyl N,N-diisopropylchloro-phosphoramidite, $[(CH_3)_2CH]_2NP(Cl)OCH_2(CH_2)CN$. Such reagents are useful in the synthesis of phosphate diester coupled non-nucleotide-oligomers.

C0 $^1$ H NMR, $CDCl_3$, 0.9–1.3 (18 protons of 6 $CH_3$'s), 3.11 ($CH_2$ of Fmoc), 3.78 (2 $CH_3$'s of DMT), 4.42 ($CH_2$—O-DMT), 4.98 (NH), 6.8–7.8 (21 aromatic protons).

C4 $^1$H NMR, $CDCl_3$, 0.9–1.2 (18 protons of 6 $CH_3$'s), 1.88 ($CH_2$), 2.21 ($CH_2$), 3.08 ($CH_2$ of Fmoc), 3.80 (2 $CH_3$'s of DMT), 4.36 ($CH_2$—O-DMT), 5.16 (NH), 5.75 (NH), 6.8–7.8 (21 aromatic protons).

C6 $^1$H NMR, $CDCl_3$, 0.9–1.2 (18 protons of 6 $CH_3$'s), 1.18–2.2 (4 $CH_2$'s), 3.07 ($CH_2$ of Fmoc), 3.78 (2 $CH_3$'s of DMT), 4.42 ($CH_2$—O-DMT), 5.6 and 6.21 (2 NH), 6.8–7.8 (21 aromatic protons).

(VIII) Methylphosphinylation of the Secondary Hydroxyl Moiety of a Non-Nucleotide Reagent Having a C6-Bridging Moiety A 4 mmol portion of a dimethoxytrityl (DMT)-blocked non-nucleotide reagent having a C6 bridging moiety (prepared according to the methods described herein) was dried by co-evaporation with dry pyridine. The residue was dissolved in 20 ml of anhydrous dichloromethane. Under a closed argon atmosphere, 1.5 equivalents of N,N-diisopropylethylphosphonamidic chloride [$(CH_3)_2CH]_2NP(Cl)OCH_3$] was added dropwise. The reaction mixture was then worked up using the procedures described above in (VII) to give 3.2 mM of the above-identified product.

$^1H$ NMR in $CDCl_3$, 6 ppm: 1–1.5 (5 methyl and 1 methylene), 1.42 ($CH_2$), 1.73 and 1.73 (2 $CH_2$), 2.21 ($CH_2$—N), 3.15 ($CH_2$—C=O), 3.78 (2 $CH_3$ of DMT), 6.80–7.85 (21 aromatic protons). Other proton signals present were not assigned.

(IX) Preparation of a Phosphate Diester Oligomer Which Incorporates a Methoxyphosphoramidite Non-Nucleotide Reagent Having a C8 Bridging Moiety A phosphate diester oligodeoxyribonucleotide was synthesized which incorporated a C8 methoxyphosphoramidite non-nucleotide reagent in the following sequence:

5'-TTT-AAG-CAG-AGT-TCA-AAA-GCC-CTT-CAG-CG-(C8-Bridging Moiety)-T-3' was prepared according to the following procedure.

The C8 methoxyphosphoramidite non-nucleotide reagent (1-O-dimethoxytrityl-2-N[N'-(N"-fluorenyl-methoxycarbonyl-6-aminohexanoyl)-2-aminoacetyl]-3-O-[N,N-diisopropyl-methoxy-phosphinyl]-2-amino-1,2-dihydroxybutane) was dissolved in dry acetonitrile at a concentration of 100 mM and coupled into the oligonucleotide sequence using a Biosearch Model 8750 DNA synthesizer by standard phosphoramidite chemistry (M. H. Caruthers et al., Methods of Enzymol. 154:287–313 (1985)) according to the manufacturer's recommendations. The 5'dimethoxytrityl protecting group was left on at the end of the synthesis to permit purification of a Sep-Pak™ C18 cartridge (Millipore/Waters, Bedford, Mass.) as described by K. M. Lo et al. (1984, Proc. Natl. Acad. Sci. USA, 81, pp. 2285–2289). During this procedure, the dimethoxytrityl protecting group was removed.

(X) Preparation of Methylphosphonate Oligomers Which Incorporate Non-Nucleotide Reagents (a) Preparation of Methylphosphonate Oligomers Methylphosphonate oligomers which incorporated non-nucleotide reagents were synthesized using methylphosphonamidite monomers and non-nucleotide methylphosphonamidite non-nucleotide reagents, according to chemical methods described by P. S. Miller et al. (1983, Nucleic Acids Res., 11, pp. 6225–6442), A. Jager and J. Engels (1984, Tetrahedron Lett., 25, pp. 1437–1440), and M. A. Dorman et al. (1984, Tetrahedron, 40, pp. 95–102). Solid-phase synthesis was performed on a Biosearch Model 8750 DNA synthesizer according to the manufacturer's recommendations with the following modifications: "G" and "C" monomers were dissolved in 1:1 acetonitrile/dichloromethane at a concentration of 100 mM. "A" and "T" monomers were dissolved in acetonitrile at a concentration of 100 mM. Non-nucleotide bridging moiety reagents were dissolved in acetonitrile at a concentration of 120 mM. DEBLOCK reagent=2.5% dichloroacetic acid in dichloromethane. OXIDIZER reagent=25 g/L iodine in 2.5% water, 25% 2,6-lutidine, 72.5% tetrahydrofuran. CAP A=10% acetic anhydride in acetonitrile. CAP B=0.625% N,N-dimethylaminopyridine in pyridine. The 5'-dimethoxytrityl protecting group was left on at the end of the synthesis to facilitate purification of the oligomers, as described below.

The crude, protected non-nucleotide reagent incorporating methylphosphonate oligomers were removed from the solid support by mixing with concentrated ammonium hydroxide for two hours at room temperature. The solution was drained from the support using an Econo-Column™ (Bio-Rad, Richmond, Calif.) and the support was washed five times with 1:1 acetonitrile/water. The eluted oligomer was then evaporated to dryness under vacuum at room temperature. Next, the protecting groups were removed from the bases with a solution of ethylenediamine/ethanol/acetonitrile/water (50:23.5:23.5:2.5) for 6 hours at room temperature. The resulting solutions were then evaporated to dryness under vacuum.

(b) Purification of Bridging Moiety-Iodified Methylphosphonate Oligomers

The 5'-dimethoxytrityl (trityl) containing oligomers were purified from non-tritylated failure sequences using a Sep-Pak™ C18 cartridge (Millipore/Waters, Bedford, Mass.) as follows: the cartridge was washed with acetonitrile, 50% acetonitrile in 100 mM triethylammonium bicarbonate (TEAB, pH 7.5), and 25 mM TEAB. Next, the crude methylphosphonate oligomer was dissolved in a small volume of 1:1 acetonitrile/water and then diluted with 25 mM TEAB to a final concentration of 5% acetonitrile. This solution was then passed through the cartridge. Next, the cartridge was washed with 15–20% acetonitrile in 25 mM TEAB to elute failure sequences from the cartridge. The trityl-on oligomer remaining bound to the cartridge was then detritylated by washing with 25 mM TEAB, 2% trifluoroacetic acid, and 25 mM TEAB, in that order. Finally, the trityl-selected oligomer was eluted from the cartridge with 50% acetonitrile/water and evaporated to dryness under vacuum at room temperature.

The bridging moiety-modified methylphosphonate oligomers obtained from the previous step, above, were further purified by reverse-phase HPLC chromatography as follows: A Beckman System Gold HPLC was used with a Hamilton PRP-1 column (Reno, Nev., 10 μ, 7 mm i.d.×305 mm long). Buffer A=50 mM triethylammonium acetate (pH 7); Buffer B=50% acetonitrile in 50 mM triethylammonium acetate (pH 7). The sample, dissolved in a small volume of 10–50% acetonitrile/water, was loaded onto the column while flowing at 2.5–3 ml/minute with 100% Buffer A. Next, a linear gradient of 0–70% Buffer B was run over 30–50 minutes at a flow rate of 2.5–3 ml/minute. Fractions containing full-length non-nucleotide reagent incorporating methylphosphonate oligomer were evaporated under vacuum and resuspended in 50% acetonitrile/water.

The target strand and the cleavage compound were as follows:

RNA oligonucleotide=5'-CAG-GAG-C- U -A-AGG-AAG-CUA-3' (R197-1) [SEQ ID NO:2]

MP-oligonucleoside=3'-GTC-CTC-G(C2) T-TCC-TTC-GAT-5' (1719-1) [SEQ ID NO:25]

The C2 bridging moiety does not contain a base which is capable of hydrogen bonding. It was discovered that, in this circumstance, the neighboring (upstream and downstream) base pairs would stack and that the opposing uridine base and C2 bridging moiety would loop out of the heteroduplex.

The RNA oligonucleotide R197-1 was labelled with $^{32}p$ according to Example 1. Hydrolysis reactions containing $^{32}$P-labelled R197-1 in 1M ethylenediamine-HCl (pH 7) were prepared in the presence and absence of C2-modified MP-oligonucleoside 1719-1 as described in Example 2. These reactions were run at 25° C for 46 hours as described in Example 2 and aliquots were analyzed by polyacrylamide gel electrophoresis as described in Example 1. Samples not containing MP-oligonucleoside 1719-1 exhibited a moderate level of hydrolysis (about 25%) consistent with the results described in Example 2. On the other hand, samples containing MP-oligonucleoside 1719-1 showed a strong cleavage band at position #8, corresponding to the location of the uridine base. Furthermore, the intensity of this band was about 10-fold greater than the same band resulting from samples incubated without MP-oligomer. This demonstrates that the RNA strand is significantly more reactive at the site of a looped-out base in a heteroduplex when compared to single-stranded RNA alone. Furthermore, the looped-out base occurs at the site of the C2-linker replacement, as predicted.

The following examples describe the direct conjugation of cleavage moieties to the non-nucleotide, non-complementary bridging portion of an otherwise-complementary methylphosphonate cleavage oligonucleoside. When hybridized to the RNA target strand, the cleavage compounds direct a "looped-out" base on the RNA strand. The following examples also describe a method for attaching cleavage moieties to an oligonucleoside such that the moieties can promote cleavage of a complementary RNA strand following formation of a heteroduplex. In these compounds, the catalytic moiety reaches over to the RNA strand and catalyzes a cleavage reaction. While it is believed that cleavage occurs via an in-line displacement reaction as described above, other mechanisms are possible and it is not intended that the present invention be limited to the mechanism of an in-line displacement reaction.

EXAMPLE 4

Preparation of Cleavage Moiety Conjugars for Attachment to an Oligonucleoside

In this example, cleavage moiety conjugars having the following structures were prepared for later attachment to an oligonucleoside:

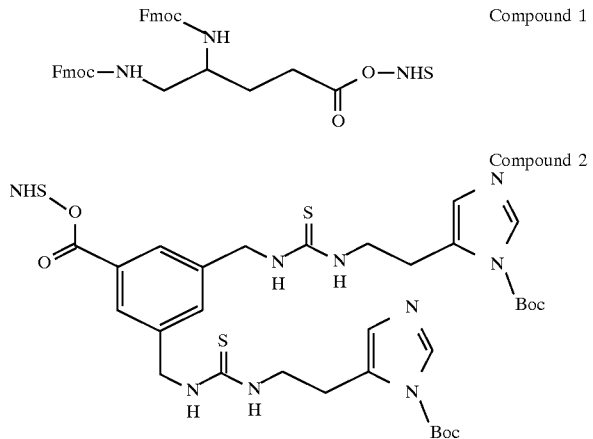

The N-hydroxysuccinimide (NHS) groups in these conjugars act as leaving groups when the conjugars are coupled to, for example, a primary amine group on the oligonucleoside portion of the eventual cleavage compound. The protecting groups (9-fluorenylmethoxycarbonyl [Fmoc] and tert-butoxycarbonyl [Boc]) may be removed following coupling.

Compound 1, an ethylene diamine (EDA) based cleavage moiety conjugar, was prepared as follows. First, t-butyl pent-4-enoate (2) was prepared by adding concentrated perchloric acid (4 drops) to a solution of pentenoic acid (10 g) in t-butyl acetate (120 mL). The reaction was stirred for 16 h at room temperature. The reaction was quenched by the addition of aqueous saturated sodium bicarbonate solution (100 mL) and stirred for 15 min. The phases were separated and the organic phase was further washed with sodium bicarbonate solution (3×100 mL), dried (MgSO$_4$), filtered and concentrated to give 8.4 g crude ester. The ester was distilled, b.p. 51°–55°/20 Torr (lit. 51°–53°/20 Torr) to give 6.4 g of the desired intermediate ester 2.

Tert-butyl 4,5-dihydroxypentanoate (3) was prepared as the next intermediate. To a solution of N-methylmorpholine oxide (2.50 g, 1.1 equiv.), acetone (3 mL) and water (8 mL) was added a solution of osmium tetroxide (20 mg, x equiv.) in t-butanol (1.5 mL) followed by ester 2 (3.00 g, 1 equiv.). The heterogeneous reaction mixture was stirred at room temperature for 16 h. A slurry of sodium hydrosulfite (330 mg), magnesium silicate (3.0 g) and water (25 mL) was prepared and added to the reaction mixture and stirred for 5 min. The reaction mixture was filtered through celite and the filtrate was extracted with ethyl acetate (2×50 mL). The combined organic extracts were dried (MgSO$_4$), filtered and concentrated to give 2.95 g of a clear viscous oil (yield 80%); PMR: 2.41 (t, 2 H), 1.45 (s, 9 H); IR 1728 (s), 3402(br m) cm$^{-1}$; MS(ESI, m/z) 191 (theoret. 190.24).

Tert-butyl 4,5-bistosyloxypentanoate (4) was prepared next. To a solution of diol (1.0 g) and triethylamine (3.0 mL) in dichloromethane (20 mL) cooled to 0° was added drop-wise a solution of tosyl chloride (2.10 g) in dichloromethane (15 mL). Following addition the reaction mixture was stirred at 0° for 30 min then at room temperature for 16 h. The solvent was removed and the residue was treated with ethyl acetate (50 mL) and water (35 mL). The organic phase was separated and washed with saturated sodium bicarbonate solution and brine (30 mL each), dried (magnesium sulfate), filtered and concentrated to give 2.92 g of a colorless oil. Chromatographic purification on silica gel and hexane/ethyl acetate (3/1) as eluant yielded 1.76 g (67% yield) of ditosylate 4; PMR: 4.66 (m, 1 H), 2.17 (dt, 2 H), 1.83 (dt, 2 H) 1.35 (s, 9 H); MS(ESI, m/z) 499 (theoret. 498.61).

Tert-butyl 4,5-diazidopentanoate (5) was prepared next. To a solution of ditosylate 4 (3.5 g, 1 equiv) in DMF (20 mL) was added sodium azide (0.936 g; 2.05 equiv) and the reaction mixture was heated at 600 for 16 h. The reaction mixture was cooled to room temperature and the solvent was removed under reduced pressure. The residue was partitioned between ethyl acetate (30 mL) and water (20 mL) and the organic phase was separated and further washed with water (30 mL), dried (magnesium sulfate), filtered and concentrated to give 1.5 g (88% crude yield) of diazide 5 as a colorless oil; PMR: 3.60 (m, 1 H), 3.45 (m, 2 H), 2.4 (t, 2 H), 1.8 (m, 2 H) and 1.46 (s, 9 H); IR 2104 (s), 1727 (m).

Tert-butyl 4,5-diaminopentanoate (6) was prepared next. A solution of diazide 5 (380 mg) in MeOH (3 mL) was added to a prehydrogenated mixture of 10% palladium on carbon (20 mg) in MeOH (5 mL). The mixture was placed under an atmosphere of hydrogen and stirred at room temperature for 3 h. The catalyst was removed by filtration through celite and the filtrate was concentrated to give 282 mg (97% crude yield) of the desired diamine 6 as a colorless oil which was used without further purification; PMR CDCl$_3$ 2.3 (m, 2 H), 1.43 (s, 9 H); IR 1721 (s), 3300 (br m).

Tert-butyl 4,5-bis(fluorenylmethoxycarbamato) pentanoate (7) was prepared next. To a solution of diamine 6 (50 mg, 1 equiv) in dichloromethane (2 mL) was added a solution of FMOC-OSu (188 mg, 2.1 equiv) in dichloromethane (2 mL) at room temperature. The reaction mixture was stirred for 16 h and the solvent was removed under reduced pressure and the residue was partitioned between ethyl acetate (10 mL) and water (10 mL). The phases were separated and the organic phase was dried (magnesium sulfate), filtered and concentrated to give 260 mg of a white solid. The desired biscarbamate 7 was isolated by flash chromatography on silica gel using hexanes/ethyl acetate (2/1) as eluant. Yield was 120 mg of a white crystalline solid (yield 71%); 3.7 (m, 1 H), 3.3 (br t, 2 H), 2.3 (t, 2 H) 1.43 (s, 9 H).

Tert-butyl 4,5-Bis(fluorenylmethoxycarbamato)pentanoic acid (8) was prepared next. Ester 7 (60 mg) was treated with a trifluoroacetic acid/dichloromethane (1/1; 4 mL) solution. The reaction mixture was stirred at room temperature for 3 h. The solvent was removed under reduced pressure and the residue was treated with ethyl acetate (4 mL) which caused some precipitation. The heterogeneous mixture was placed in the freezer overnight and the solids were isolated by filtration to give 35 mg of desired acid 8 (64% yield); PMR 3.7 (m, 1 H), 2.3 (t, 2 H); MS(ESI, m/z) 577.5 (theoret. 576.65).

The final EDA-based, protected cleavage moiety conjugar succinimidyl 4,5-bis(fluorenylmethoxycarbamato) pentanatoate (Compound 1) was then prepared. To a solution of acid 8 (20 mg, 1 equiv) in dioxane (1 mL) and triethylamine (5.6 uL, 1.1 equiv) was added dropwise a solution of succinimidyl 1,2,2,2-tetrachloroethylcarbonate (11 mg, 1 equiv) in dioxane (1 mL). The reaction mixture was stirred at room temperature for 3 h. The reaction mixture was concentrated to dryness and the residue was dissolved in ethyl acetate (10 mL) and washed with 10% aqueous citric acid, saturated aqueous sodium bicarbonate and brine (10 mL each), dried (magnesium sulfate), filtered and concentrated to give 25 mg of a white solid that was recrystallized from hexaneslethyl acetate to give 16 mg (68% yield) of desired succinimidyl ester (Compound 1) as a white crystalline solid; PMR CDCl$_3$ 3.76 (m, 1 H), 3.30 (t, 2 H), 2.82 (s, 4 H), 2.68 (t, 2 H); MS(ESI, m/z) 674.4 (theoret. 673.7)

Compound 2, another EDA-based cleavage moiety conjugar, was prepared as follows. First, the intermediate methyl 3,5-bis(isothiocyanatomethyl)benzoate (12) was synthesized. To a solution of methyl 3,5-bis(bromomethyl) benzoate (1.0 g, 1 equiv.) in dimethylformamide (20 mL) at room temperature was added sodium azide (0.40 g, 2 equiv.) and the reaction mixture was heated by an oil bath at 70° C. for 15 min. The reaction mixture was allowed to cool to room temperature and then concentrated under reduced pressure to give an oily solid residue. The residue was partitioned between ethyl acetate and water. The organic phase was washed three times with water, once with brine, dried (MgSO$_4$), filtered and concentrated under reduced pressure to afford 0.77 g of methyl 3,5-bis(azidomethyl) benzoate (10) as a yellow oil. The crude product was used without further purification; R$_f$ 0.42 (4:1 hexane-ethyl acetate); IR (thin film): 2953, 2102, 1724, 1435, 1307, 1224 cm$^{-1}$; PMR δ7.97 (s, 2 H), 7.49 (s, 1 H), 4.45 (s, 4 H), 3.95 (s, 3 H).

A stirred suspension of crude 10 (0.77 g) and 10% Pd on carbon (0.07 g) in methanol (5 mL) was degassed at room temperature and then subjected to 1 atm of hydrogen gas via inflated balloon for 12 h. Excess hydrogen was removed under vacuum and the reaction vessel was purged with argon. The reaction mixture was filtered through filter agent Celatom FW-14 with methanol washings to remove catalyst. The filtrate was concentrated under reduced pressure to provide 0.60 g of methyl 3,5-bis(aminomethyl)benzoate (11) as a pale yellow oil. The crude product was used without further purification; IR(thin film): 3357, 3296, 2951, 1721, 1651, 1602, 1544, 1435, 1307, 1224 cm$^{-1}$; PMR (DMSO-d$_6$) δ7.76 (s, 2 H), 7.56 (s, 1 H), 3.85 (s, 4 H), 3.79 (s, 3 H).

To a stirred suspension of crude 11 (0.60 g) in a 1:1 mixture of toluene-water (20 mL) was added sodium carbonate (0.83 g, 7.80 mmol). The mixture was cooled in an ice-water bath and then thiophosgene (0.52 mL, 6.86 mmol) was added dropwise via syringe. The reaction gradually warmed to room temperature and was allowed to stand overnight. The resulting bilayer was extracted with ethyl acetate. The organic extracts were washed with saturated aqueous sodium bicarbonate solution and then with brine, dried (MgSO$_4$), filtered and concentrated under reduced pressure to give a yellow oil. Purification by flash chromatography on silica gel (230400 mesh) using 9:1 hexane-ethyl acetate, then 7:3 hexane-ethyl acetate as eluant provided 0.39 g of 12 as a thick oil which solidified upon standing in a refrigerator; yield 43% (three steps); mp 67°–69° C.; IR(thin film): 2950, 2185, 2096, 1722, 1609, 1434, 1305, 1222 cm$^{-1}$; PMR δ7.95 (s, 2 H), 7.48 (s, 1 H), 4.81 (s, 4 H), 3.93 (s, 3 H).

The final protected cleavage moiety conjugar bis-thiourea succinimidyl ester (Compound 2) was then prepared. To a solution of methyl 3,5-bis(isothiocyanatomethyl)benzoate (12) (0.20 g, 1 equiv.) in THF (4 mL) at room temperature were added histamine dihydrochloride (0.26 g, 2 equiv.) and 1M sodium carbonate solution (1.4 mL, 2 equiv.). The resulting biphasic mixture was heated at 45° C. for 5 h using a heated water bath. The reaction mixture was transferred to a separatory funnel and the phases were separated. The organic phase was concentrated under reduced pressure to give a wet oily residue. The crude residue was dissolved in methanol (3 mL) and then treated with 1M sodium hydroxide solution (1.1 mL, 1.1 mmol). The reaction mixture was heated at 40° C. for 4 h using a heated water bath. The reaction was concentrated under reduced pressure to afford bis-thiourea carboxylic acid (13) as an oily residue.

The crude residue was dissolved in dioxane (3 mL) and treated with di-tert-butyldicarbonate (0.47 g, 2.16 mmol). The reaction was stirred at room temperature for 12 h, diluted with water (5 mL) and extracted with ethyl acetate to remove neutrals. The aqueous phase was acidified to pH 3 using 3M HCl solution and extracted with ethyl acetate. Organic extracts were washed with brine, dried (MgSO$_4$), filtered and concentrated under reduced presssure to provide 0.20 g of carboxylic acid 14 as a crude white solid. PMR (acetone-d$_6$) δ8.00 (s, 2 H), 7.93 (s, 1 H), 7.54 (br s, 2 H), 7.26 (s, 2 H), 4.82 (br s, 4 H), 3.79 (br m, 4 H), 2.80 (t, J=6.8 Hz, 4 H), 1.6 (s, 18 H).

To a solution of crude carboxylic acid 14 (0.20 g) in methylene chloride (4 mL) were added dicyclohexylcarbodiimide (0.069 g, 0.33 mmol) and N-hydroxysuccinimide (0.038 g, 0.33 mmol). The reaction mixture was stirred at room temperature for 4 h and then filtered to remove the urea byproduct. The filtrate was concentrated under reduced pressure to give a semi-solid residue. Purification by flash chromatography on Fluorisil using 24:1 methylene chloride-isopropanol as eluent provided 49 mg of succinimidyl ester (Compound 2) as a white solid; yield 9% (four steps); mp 100 ° C. (dec.). PMR δ7.95 (s, 2 H), 7.90 (s, 2 H), 7.59 (s, 1 H), 7.14 (s, 2 H), 4.74 (br m, 4 H), 3.67 (br m, 4 H), 2.90 (s, 4 H), 2.72 (t, j=6.0 Hz, 4 H), 1.60 (s, 18 H). MS(ESI, m/z) 784.4 (MH$^+$), 684.4, 584.4.

The NMR, FTIR and MS data given in the examples above were obtained as follows:

$^1$H NMR spectra were recorded on a 300 MHz Bruker ARX 300 Spectrometer. All $^1$H results were obtained in CDCL3 unless otherwise indicated. FTIR spectra were recorded on a Mattson Galaxy Series FTIR 3000 spectrometer. Mass spectra were recorded on a Fisons Trio 2000 Spectrometer and provided by JBL Scientific of San Luis Obispo, Calif. NMR, FTIR and MS spectra were consistent with assigned structure.

The oligonucleosides used in the following examples were as follows:

RNA oligonucleotide=5'-CAG-GAG-C- U -A-AGG-AAG-CUA-3' (R197-1) [SEQ ID NO:2]

MP-oligonucleoside=3'-GTC-CTC-G(C2) T-TCC-TTC-GAT-5' (1719-1) [SEQ ID NO:25]

EXAMPLE 5

Preparation of MP-oligonucleoside Conjugates of 1719-1 With Catalytic Cleavage Moieties 1, 2 and 3

The corresponding oligonucleoside-conjugates having the catalytic moieties provided by compounds 1 and 2 (Example 4) were as follows:

2337-1=Oligonucleoside conjugate of 1719-1 and Compound 1 (EDA)

2437-1 =Oligonucleoside conjugate of 1719-1 and Compound 2 (Bis-imidazole)

In addition, a third cleavage moiety conjugar (Compound 3), containing a histidine-lysine dipeptide cleavage portion, was prepared for conjugation with oligonucleoside 1719-1 as follows:

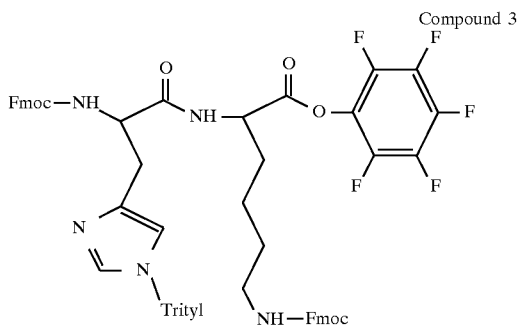

Compound 3

Fmoc = 9-flourenylmethoxycarbonyl
NHS = N—hydroxysuccinimide 2435-1 = Oligonucleoside conjugate of 1719-1 and compound 3 (His—Lys)

The abbreviations EDA, Bis-imidazole and His-Lys refer to the cleavage moieties alkyl-ethylenediamine, bis-(alkylthiourea-histidine)-isophthalate, and histidine-lysine dipeptide, respectively.

The general method for coupling compounds 1, 2 or 3 onto MP-oligonucleoside 1719-1 was as follows.

(a) Conjugation reactions. Approximately 60 $A_{260}$ units of MP-oligonucleoside 1719-1 was added as a solution in 1:1 acetonitrile/water to a sterile polypropylene microcentrifuge tube and lyophilized in a Speed-Vac™ microevaporation apparatus (Savant, Inc.). The resulting powder was resuspended in 1:1 acetonitrile/water (100 μL). Next, the following reagents were added in the order indicated with mixing after each addition to avoid precipitation: dimethylsulfoxide (DMSO, 215 μL), 1M aqueous HEPES buffer (pH 8.0, 50 μL), 1:1 acetonitrile/water (100 μL), and a 100 mM solution of either Compound 1, Compound 2 or Compound 3 in anhydrous DMSO (35 μL). The resulting mixture was reacted at room temperature for approximately 1 hour. At the end of this time period, additional aliquots of 100mM Compound 1, Compound 2, or Compound 3, respectively (in DMSO, 12.5 μL), DMSO (12.5 μL), 1M HEPES (pH 8.0, 5 μL) and sterile water (20 μL) were added. After mixing, the reaction was allowed to continue for an additional 1 hour. Absolute ethanol (1 mL) was added and the tube was chilled at −20° C. to precipitate the conjugated product oligonucleoside. Then, the tube was centrifuged for 15 minutes in a microcentrifuge at 4° C. The supernatant was discarded and the resulting pellet was resuspended in 1:1 acetonitrile/water (400 μL).

(b) HPLC analysis and purification. HPLC chromatography was conducted on the crude products to determine purity as follows. A Beckman System Gold HPLC system equipped with a Model 168 diode array detector was used in a dual gradient mode with Solvent A—100 mM ammonium acetate (pH 6) and Solvent B—acetonitrile. A Hamilton PRP-1 polymeric reversed-phase column was used (4.1 mm×250 mM). The elution profiles were as follows: Program #1 (for compounds 2337-1 and 2437-1): 0–15% Solvent B (0–8 minutes) and then 15–40% (8–38 minutes); or Program #2 (for compound 2435-1): 0–15% Solvent B (0–8 minutes) and then 15–70% Solvent B (8–60 minutes).

| | | |
|---|---|---|
| 1719-1 | 16.2 minutes | (Program #1) |
| 1719-1 | 17.3 minutes | (Program #2) |
| 2337-1 (protected*) | 32.9 minutes | (Program #1) |
| 2435-1 (protected*) | 40.6 minutes | (Program #2) |
| 2437-1 (protected*) | 31.2 minutes | (Program #1) |

*Retention times correspond to the protected forms of these conjugates; in other words, Fmoc protecting groups remain on 2337-1 and 2435-1, a trityl protecting group remains on 2435-1, and Boc protecting groups remain on 2437-1.

The protected forms of 2337-1, 2435-1 and 2437-1 were purified by preparative HPLC chromatography using the same conditions described above for the analytical runs, except that the flow rates were changed to 1.5 mL/minute and the peaks were monitored at 297 nm instead of 260 nm to keep the data within the response range of the diode-array detector. Samples were injected in multiple aliquots (50 μL) at 1 minute intervals using a 500 μL sample loop with 100% Solvent A flowing through the column at 1.5 mL/minute. After the last aliquot was loaded onto the column, the appropriation elution profile was run and the product peaks were collected manually into sterile polypropylene culture tubes. The resulting product peaks were then concentrated to dryness using a Speed-Vac™ apparatus as described above.

(c) Removal of protecting groups. Removal of the protecting groups from each oligonucleoside conjugate was achieved as follows. Compounds 2337-1 and 2437-1: The dried product peaks from preparative HPLC purification (see above) were resuspended in 47.5% acetonitrile/47.5% ethanol/5% water (1 mL) and redistilled ethylenediamine (1 mL) was added. The contents of each t were mixed by vortexing and then allowed to stand at room temperature for 1 hour. Next, the solutions were diluted with water (9 mL) and neutralized with glacial acetic acid (600 μL). These solutions were then applied to a Sep-Pak™ C18 cartridge (Millipore Corp.) that had been previously washed with acetonitrile (5 mL), 1:1 acetonitrile/water (5 mL) and water (5 mL). After application of the samples, the cartridges were washed with water (8 mL). The cartridges were then eluted with 1:1 acetonitrile/water (5 mL) and the eluents were collected into sterile polypropylene culture tubes. These solutions were then dried in a Speed-Vac™ apparatus as described above. Compound 2435-1: The dried product peak from preparative HPLC was treated with 47.5% acetonitrile/47.5% ethanol/5% water (1 mL) and redistilled ethylenediamine (1 mL) and then loaded onto a Sep-Pak™ (C18 cartridge exacted as described above. The cartridge was then washed with water (8 mL) and acidified with 2% aqueous trifluoroacetic acid (5 mL) and the product was eluted with 1:1 acetonitrile/water (5 mL), collected into a sterile polypropylene culture tube and dried down as described above.

Following removal of the protecting groups, the oligonucleoside conjugates were purified by a second round of preparative HPLC as described above. Retention times for the final products were as follows:

| | | |
|---|---|---|
| 2337-1 (unprotected): | 15.7 minutes | (Program #1) |
| 2435-1 (unprotected): | 23.6 minutes | (Program #2) |
| 2437-1 (unprotected): | 20.8 minutes | (Program #1) |

(d) Mass-spectral analysis. Confirmation of the identity of each oligonucleoside conjugate was obtained by electrospray ionization mass spectrometry. The theoretical and experimental values for the mass of each oligonucleoside conjugate are reported below:

| | | |
|---|---|---|
| 2337-1: | Theoret. 5408 amu | Found: 5407.9 amu |
| 2435-1: | Theoret. 5559.3 amu | Found: 5560.5 amu |
| 2437-1: | Theoret. 5762.0 amu | Found: 5763.9 amu |

EXAMPLE 6

Demonstration of Site-Directed Cleavage of a Synthetic RNA Target by Oligonucleoside Cleavage Compounds 2337-1, 2435-1 and 2437-1

(a) Labelling RNA target with $^{32}$p. RNA oligonucleotide R197 (20 pmols) was reacted with [γ-$^{32}$P] ATP (3000 Ci/mmol, 50 μCi) in 20 μL of 1× kinase buffer (USB, Inc.) and 3 units of T4-polynucleotide kinase (USB, Inc.). The reaction was run at 37° C. for 30 minutes. Next, the $^{32}$P-labelled RNA oligonucleotide was purified on a Nensorb-cartridge (NEN/Dupont, Inc.) according to the protocol recommended by the manufacturer. The product oligonucleotide was eluted from the cartridge with 50% aqueous methanol (500 μL) and stored at 4° C.

(b) Incubation with oligonucleoside cleavage compounds. $^{32}$P-labelled RNA oligonucleotide R197 (approximately 250,000 cpm) was incubated with either of MP-oligonucleoside 1719-1 (control), or MP-oligonucleoside cleavage compounds 2337-1, 2435-1 or 2437-1 (75 μM) in 20 mM potassium phosphate buffer (pH 7.2), 100 mM NaCl, 1 mM EDTA and 0.03% sarcosylate. The incubations were conducted at 25° C. over periods ranging from 2–5 days.

(c) Analysis of cleaved RNA by gel electrophoresis. Aliquots from the incubation reactions (2 μL) were diluted with 90% formamide/89 mM Tris-borate (pH 8.3), 25 mM disodium EDTA (1× TBE buffer) containing 0.1% bromphenol blue marker dye. The resulting samples were loaded onto a 20% polyacrylamide/bisacrylamide (19:1)/1× TBE/7M urea gel (0.5 mm thick×20×30 cm). A current of approximately 1500 volts was then applied to the gel over a period of about 1.5 hours. The wet gel was then exposed to Type XAR-5 x-ray film (Eastman Kodak, Inc.) for about 1–2 hours at −20° C. Bands corresponding to full-length (uncleaved) RNA were observed in each of the lanes. There were also faint bands corresponding to cleaved RNA in the lanes corresponding to incubations with MP-oligonucleoside cleavage compounds 2337-1, 2435-1 or 2437-1. After 5 days, the levels of cleavage estimated from band intensities for the conjugates were approximately 1–2% (for conjugate 2337-1) and approximately 8–10% (for conjugates 2435-1 and 2437-1), respectively. The location of the cleavage product on the gel was consistent with the intended target site at the position of the "looped-out" base. No detectable cleavage was observed with the control (unconjugated) MP-oligonucleoside 1719-1.

The examples described above clearly illustrate that site-directed cleavage of RNA is possible by conjugating a catalytic cleavage moiety directly onto the antisense oligonucleoside, in this case at a position corresponding to the non-complementary portion of the cleavage compound.

EXAMPLE 7

Attachment of an Ethylenediamine-Based Cleavage Moiety to a Methylphosphonate Oligonucleoside Having an Internal Cytosine Based Modified With an Amino-Linker A modified form of cytosine having an amino linker at the C4 position ("ethylamineC") was developed for coupling cleavage catalysts to methylphosphonate oligonucleosides:

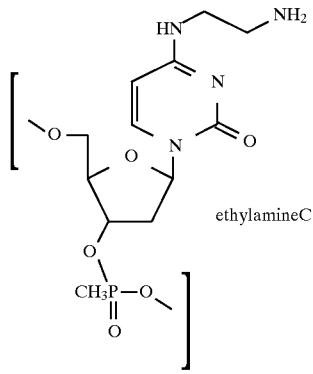

ethylamineC

This linker modification provides one method for attaching a cleavage moiety directly to an oligonucleoside base (including a base that is complementary to a nucleotide on the RNA target strand) and directing the cleavage moiety toward the complementary target strand. In this case, a base on the RNA strand located in either the 5'- or 3'-direction with respect to the ethylamineC moiety can be rotated out of the heteroduplex by, for example, simply omitting a complementary base on the antisense strand. In this case, the rotated base on the RNA strand will "bulge" out from the heteroduplex structure, as illustrated for example in the following diagram (C* represents the internal cytosine base modified with the ethylamineC linker with an attached cleavage moiety):

3'-AUCGAAGG    AAUCGAGGAC-5'  (R336)[SEQ ID NO: 4]
5'-TAGCTTCC*    TTAGCTCCTG-3'  (2338-1)[SEQ ID NO: 26]

Here, the modified cytosine portion of C* is still capable of hydrogen bonding to the complementary guanine base on the RNA target strand. Likewise, the thymine base on the 3'-side of the C* unit is capable of hydrogen bonding to a complementary adenine base as shown. However, the uridine nucleotide on the target strand is bulged out from the heteroduplex because its uracil base has no complementary base in the methylphosphonate oligonucleoside and, moreover, because the G and A nucleotides on either side of the uridine have been pulled closer together in order to hybridize with the -C*T- "non-complementary" portion in the methylphosphonate oligomer.

In the present example the cleavage moiety (an ethylenediamine moiety) in C* was attached to the ethylamineC structure using a linker arm which positions the cleavage moiety so as to effect cleavage of a phosphodiester bond of the uridine nucleotide. A preliminary ethylamineC-modified methylphosphonate oligonucleoside 2173-1 was prepared as follows. First, 4-triazolyl-5'-dimethoxytrityl-uridine was made according to the standard procedure of Frohler and Matteucci, Tetrahedron Let. 1983, 24:3171, and Webb and Matteucci, J. Am. Chem. Soc. 1986, 108:2764. 13.35 g of 4-triazolyl-5'-dimethoxytrityl-uridine was placed in a 250 ml round bottom flask, and rendered anhydrous by coevaporations with acetonitrile (ACN) (2×50 ml). The compound was redissolved in 135 ml of dry ACN, blanketed with argon and cooled in an ice bath to 0° C. To this solution 3.85 ml triethylamine (1.3 equivalents, 36 mmol) was added quickly, followed by 4.6 ml chloro-methyl-N,N-diisopropylaminophosphine (1.1 equivalents, 25 mmol) which was added dropwise with vigorous stirring. The reaction mixture was allowed to warm to room temperature for 1 hour before being analyzed by HPLC. The reaction mixture was concentrated under vacuum to an off-white foam which was then purified immediately on 140 g normal phase flash silica gel column equilibrated in 18:6:1 ethyl acetate:heptane:triethylamine. The reaction afforded 13.3 g 4-(triazolyl)-1 -(5'-dimethoxytrityl-3'-(N,N-di isopropylmethylphosphonamidite)-2'-deoxyribofuranosyl)-pyrimidin-2-one ($Ct^{trz}$) as an off-white solid foam (80% yield) with an HPLC purity of 93.8%.

The protected cyclized $C^{trz}$ methylphosphonamidite monomer was then incorporated into the oligonucleoside structure of compound 2173-1 using standard procedures. The resulting support-bound oligonucleoside was then deprotected using 1:1 EDA/ACN (50 ml) for 6.5 hrs. Deprotected oligonucleoside was then filtered from support, and neutralized to pH 7.0 with acetic acid. The neutralized solution was diluted with $H_2O$ to 10% organic content, and adsorbed to C-18 (Waters Prep.) reverse phase silica (10 g) in a filter funnel. The silica was packed into a stainless steel pre-column (20×100mm), and 50 mM $KH_2PO_4$ pH 7 (100 ml) was pumped through the column using an LC pump. The pre-column was connected in-tandem in front of a pre-equilibrated (50 mM $KH_2PO_4$ pH 7) reverse phase column (Whatman 10 ODS 3,20×250 mm), and this was attached to a Beckman 126 pump/166 detector. Full-length oligonucleoside was eluted using (A) 50 mM $KH_2PO_4$ pH 7 and (B) ACN by a gradient of 0–45% ACN over 85 min. Fractions were analyzed on an analytical reverse phase column (Whatman 5 ODS 3,4.6×100 mm); selected fractions were pooled, desalted on C-18, bottled, and lyophilized. A sample was removed for confirmation of desired compound electrospray ionization mass spectrometry analysis.

The structure of compound 2173-1 was as follows:

5 '-TAG-CTT-C(ethylamineC)T-TAG-CTC-CTG-3' (2173-1) [SEQ ID NO:26].

The ethylamineC-modified oligonucleoside 2173-1 was then reacted with the ethylenediamine (EDA) cleavage moiety reagent described in Example 4 (Compound 1) according to the procedures described in Example 5 to form the cleavage moiety-containing cleavage compound 2338-1. In the final structure, Compound 1 is bonded via an amide bond to the terminal amino group of the ethylamineC structure, and the Fmoc protecting groups are removed.

Results of electrospray ionization mass spectrometry analysis of compound 2338-1 were 5540.0 amu (theoret.) and 5539.9 amu (found).

EXAMPLE 8

Cleavage of Synthetic RNA with Chelated Zinc Complexes

The present example demonstrates that certain chelated organometallic complexes such as shown below are capable of catalyzing the cleavage of synthetic RNA oligomers:

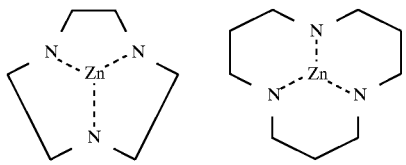

Zn[1, 4, 7-triazanonane]2+   Zn[1, 5, 9-triazadodecane]2+

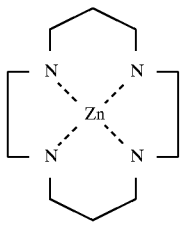

Zn[1, 4, 8, 11-tetraazatetradecane]2+

Buffered solutions of each of the zinc complexes depicted above were incubated with $^{32}P$-labelled R183 oligonucleoside and the products were analyzed by polyacrylamide gel electrophoresis as described in Example 1. Both $Zn[1,4,7-triazanonane]^{2+}$ and $Zn[1,5,9-triazadodecane]^{2+}$ were shown to completely degrade the RNA substrate to monomeric units at 50 mM concentrations (overnight incubation at 50° C.). Buffered, unchelated $Zn(NO_3)_2$ catalyzed similar cleavage at 50 mM according to the same procedure. The tetracoordinate complex $Zn[1,4,8,1 1-tetraazatetradecane]^{2+}$ failed to show any catalysis under these conditions, indicating that a tetracoordinate complex of zinc does not catalyze RNA hydrolysis.

Each of these complexes was then re-tested at 0.2 mM concentrations with 20 hour incubations at 50° C. Under these conditions, only the $Zn[1,5,9-triazadodecane]^{2+}$ complex showed any catalytic cleavage of the RNA substrate (about 40–50% of the full-length RNA was hydrolyzed to smaller fragments). Neither of the other two zinc complexes nor free uncomplexed zinc showed any appreciable cleavage. Thus, the $Zn[1,5,9-triazadodecane]^{2+}$ complex was clearly a more active cleavage catalyst than free zinc alone.

EXAMPLE 9

Site-Directed Cleavage by Organometallic Complexes of an RNA Target in the Presence of a Complementary Methylphosphonate Oligonucleoside Containing a Non-Nucleotide, Non-Complementary Bridging Portion in Place of One of the Bases The present example illustrates that chelated organometallic complexes are capable of catalyzing site-specific cleavage of an RNA substrate when hybridized to a complementary antisense oligomer containing an internal non-nucleotide bridging moiety in a "loopout" motif.

$Zn[1,5,9-triazadodecane]^{2+}$ (0.2 mM) was incubated with $^{32}P$-labelled RNA (R197-1) and MP-oligonucleoside (1719-

1) according to the procedure given in Example 3. The resulting reactions were analyzed by polyacrylamide gel electrophoresis as described in Example 1. Samples containing MP-oligonucleoside 1719-1 showed a strong cleavage band at position #8, corresponding to the location of the "looped out" uridine base. Furthermore, the intensity of cleavage at this position was greater than for the same band resulting from samples incubated without MP-oligomer.

EXAMPLE 10

Comparison of Various Catalysts for Cleavage of a Synthetic RNA Substrate with Quantification by High Performance Liquid Chromatography In this example, the hydrolysis products from a synthetic RNA substrate were separated and quantified by high performance liquid chromatography (HPLC).

The HPLC apparatus consisted of a Beckman Model 126 dual gradient solvent module equipped with a Model 168 diode array detector and an Altex Model 240A manual sample injector. The column used was a Nucleogen DEAE 60-7 (anion-exchange, 4.6 mm i.d.×100 mm long). Separation buffers were: Solvent A=25 mM Tris-acetate (pH 7.4); Solvent B=25 mM Tris-acetate (pH 7.4), 2M NaCl. Elution conditions were 040% Solvent B, 0–20 minutes; flow rate 1.5 mL/min. Peaks corresponding to the RNA oligomer and its cleavage fragments were detected by monitoring the absorbance at 260 nm.

The RNA oligomer used for this experiment was a 22-mer having the following sequence:

5'-CAU-GCA-GGA-GCU-AAG-GAA-GCU-A-3' (R320-2) [SEQ ID NO:27]

Samples containing the RNA R320-2 (0.050 $A_{260}$ units) were incubated in the presence of test catalyst in 100 mM HEPES buffer (pH 7.6) at 37° C. (total sample volume 10 $\mu$L). At various specified time intervals, individual samples were removed from incubation, frozen in dry ice/ethanol, and stored at −20° C. for analysis at a later time. Next, samples were individually removed from the freezer, thawed, diluted with Solvent A (90 $\mu$L) and analyzed immediately by HPLC according to the separation protocol described above. The peak corresponding to full-length oligomer (retention time=15.0 min.) was quantitated by integration (expressed in $mA_{260}$ units) using Beckman System Gold software with a PC computer interface. The percent of full-length RNA oligomer remaining at a specified time was determined from a ratio of peak areas for the full-length oligomer at that time versus the area at time=0. Results are summarized below:

priate adjustments for differences in concentration of each catalyst). The europium (III) complex of 1,4,7,10-tetrakis (2-hydroxyethyl)-1,4,7,10-tetraazacyclododecane (Eu [THED]) (see Morrow and Chin, *Inorg. Chem.*, 1993; 32:3357–3361) was also active in this test.

EXAMPLE 11

Preparation of Oligoribonucleosides

The oligoribonucleosides described in the preceding examples may be synthesized using procedures such as those of the present example.

The oligoribonucleosides are synthesized using 5'-O-dimethoxytrityl-2'-O-tert-butyidimethylsilyl-3'-O-N,N-diisopropyl-β-cyanoethylphosphoramidite nucleosides (purchased from either Millipore or Peninsula Laboratories). The syntheses are done on a 1 $\mu$mole scale with a Milligen 8750 automated DNA synthesizer using standard Milligen phosphoramidite procedures with the exception that the coupling times are extended to 12 minutes to allow adequate time for the more sterically hindered 2'-O-tert-butyidimethylsilyl RNA monomers to react. The syntheses are begun on control pore glass bound 2'-O-tert-butyldimethylsilyl ribonucleosides purchased from Peninsula Laboratories. All other oligonucleoside synthesis reagents are as described in Milligen's standard protocols.

After synthesis, the oligonucleosides are handled under sterile, RNase-free conditions. Water is sterilized by overnight treatment with 0.5% diethylpyrocarbonate followed by autoclaving. All glassware is baked for at least hours at 300° C.

The oligonucleosides are deprotected and cleaved from support by first treating the support-bound oligonucleoside with 3:1 ammonium hydrazide/ethanol for 15 hours at 55° C. The supernatant, which contains the oligonucleoside, is then decanted and evaporated to dryness. The resultant residue is then treated with 0.6 mL of 1M tetrabutylammonium fluoride in tetrahydrofuran (which contains 5% or less water) for 24 hours at room temperature. The reaction is quenched by the addition of 0.6 mL of aqueous 2M triethylammonium acetate, pH 7. Desalting of the reaction mixture is accomplished by passing the solution through a Bio-Rad 1ODG column using sterile water. The desalted oligonucleoside is then dried.

Purification of the oligoribonucleosides is done by polyacrylamide gel electrophoresis (PAGE) containing 15% 19:1 polyacrylamide/bis-acrylamide and 7M urea using standard procedures (see, Maniatis, T. et al., *Molecular Cloning A Laboratory Manual*, pages 184–185 (Cold Spring Harbor

TABLE 3

Degradation of R320-2 by various cleavage catalysts.

| Reagent Present | Conc. | % remaining 0 Hours | % remaining 4 Hours | % remaining 9 Hours | % remaining 21 Hours | % remaining 45 Hours |
|---|---|---|---|---|---|---|
| His—Lys dipeptide | 200 mM | NA | 13.60% | 0.81% | 0% | 0% |
| EDA | 200 mM | 96.12% | 89.49% | 84.91% | 63.01% | 42.32% |
| Eu[THED]$^{3+}$ | 0.5 mM | 98.05% | 93.73% | 69.79% | 48.73% | NA |
| Buffer control | 0.1 mM | 97.14% | NA | 97.17% | 97.46% | 96.77% |

NA = not analyzed.

According to this data, the His-Lys dipeptide is approximately 50 times more potent than EDA (making the appro- 1982)). The gels are 20 cm wide by 40 cm long and 6 mm in width. The oligoribonucleotides (60 OD Units) are dissolved in 200 μL of water containing 1.25% bromophenol blue and loaded onto the gel. The gels are run overnight at 300 V. The product bands are visualized by UV backshadowing, excised, and the product eluted with 0.5M sodium acetate overnight. The product is desalted using a Waters C18 Sep-Pak cartridge with the manufacturer supplied protocol. The product is then kinased and analyzed by PAGE.

It is evident from the results reported herein that the described oligonucleoside compounds will be effective agents for reducing or preventing expression of undesired nucleic acid. By controlling the expression of target nucleic acid, various diseases and conditions may be treated.

All publications and patent documents cited in this specification are incorporated herein by reference as if each individual document were specifically and individually indicated to be incorporated by reference.

Although the present invention has been described in some detail by way of illustration and example for purposes of clarity of understanding, it will be readily apparent to those of ordinary skill in the art in light of the teachings of this invention that various changes and modifications may be made thereto without departing from the spirit or scope of the claims. Therefore, the foregoing description should not be construed to limit the scope of the present invention, which is set forth in the appended claims.

What is claimed is:

1. An oligonucleotide cleavage compound for hybridizing to a target nucleic acid strand and effecting cleavage thereof, comprising:

an oligonucleoside sequence that is substantially complementary to a target region of the target nucleic acid strand;

a portion that is non-complementary to a target site in the target region such that, when the cleavage compound is hybridized to the target strand, a base group at said site is oriented away from an inter-strand orientation; and a cleavage moiety, wherein the cleavage moiety and the noncomplementary region are linked, selected from the group consisting of:

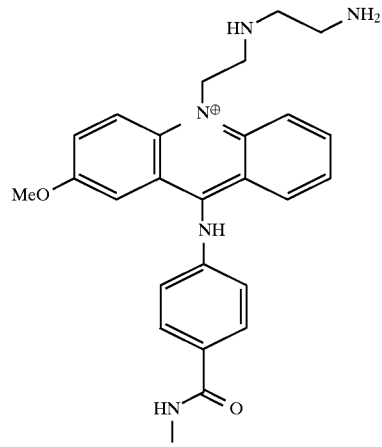

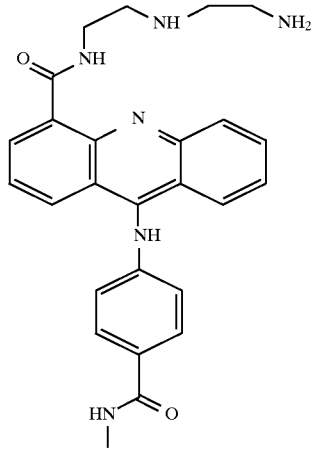

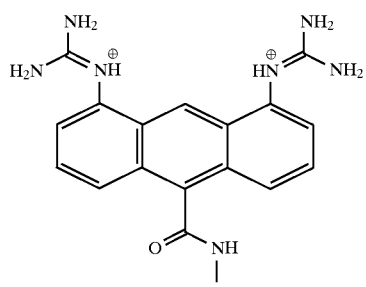

and

-continued

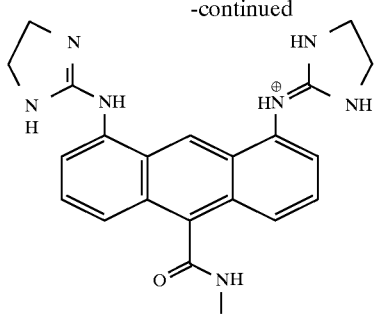

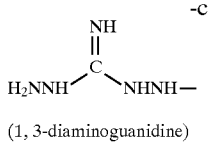

(1, 3-diaminoguanidine)

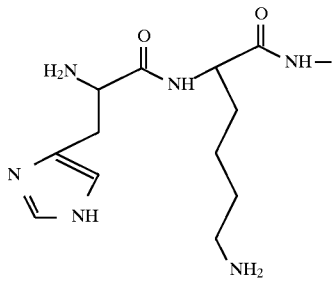

(his-lysdipeptide)

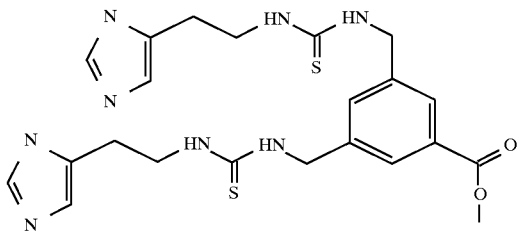

(bis-(alkylthioureahistidine)isophthalate)

2. An oligonucleotide cleavage compound for hybridizing to a target nucleic acid strand and effecting cleavage thereof, comprising:

an oligonucleoside sequence that is substantially complementary to a target region of the target nucleic acid strand;

a portion that is non-complementary to a target site in the target region such that, when the cleavage compound is hybridized to the target strand, a base group at said site is oriented away from an inter-strand orientation; and a cleavage moiety, wherein the cleavage moiety is selected from the group consisting of:

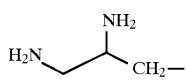 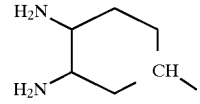

(Ethylenediamine)   (1, 2-diaminocyclohexane)

* * * * *